(12) United States Patent
Kassab

(10) Patent No.: US 8,721,718 B2
(45) Date of Patent: May 13, 2014

(54) SYSTEMS AND METHODS FOR VALVE ANNULUS REMODELING

(75) Inventor: Ghassan S. Kassab, Zionsville, IN (US)

(73) Assignee: CVDevices, LLC, Zionsville, IN (US)

( * ) Notice: Subject to any disclaimer, the term of this patent is extended or adjusted under 35 U.S.C. 154(b) by 620 days.

(21) Appl. No.: 12/521,837

(22) PCT Filed: Jan. 23, 2008

(86) PCT No.: PCT/US2008/000840
§ 371 (c)(1),
(2), (4) Date: Jun. 30, 2009

(87) PCT Pub. No.: WO2008/091614
PCT Pub. Date: Jul. 31, 2008

(65) Prior Publication Data
US 2010/0087919 A1  Apr. 8, 2010

Related U.S. Application Data

(63) Continuation-in-part of application No. PCT/US2007/015267, filed on Jun. 29, 2007.

(60) Provisional application No. 60/881,836, filed on Jan. 23, 2007.

(51) Int. Cl.
  *A61F 2/24*   (2006.01)
(52) U.S. Cl.
  USPC .......... 623/2.37; 623/2.36; 623/2.1; 623/2.11

(58) Field of Classification Search
  USPC ............ 623/2.11, 2.36, 2.37, 2.1, 2.12, 2.14, 623/2.17, 2.18, 2.38, 2.39, 2.4, 2.41
See application file for complete search history.

(56) References Cited

U.S. PATENT DOCUMENTS

| 7,166,127 | B2 * | 1/2007 | Spence et al. | 623/2.37 |
|---|---|---|---|---|
| 2004/0236170 | A1 | 11/2004 | Kim | |
| 2005/0267571 | A1 | 12/2005 | Spence et al. | |
| 2005/0288781 | A1 | 12/2005 | Moaddeb et al. | |
| 2007/0118215 | A1 * | 5/2007 | Moaddeb | 623/2.37 |
| 2007/0135913 | A1 * | 6/2007 | Moaddeb et al. | 623/2.37 |
| 2008/0300672 | A1 * | 12/2008 | Kassab et al. | 623/1.15 |

OTHER PUBLICATIONS

PCT/US2008/000840, PCT Search Report and Written Opinion, dated Jun. 18, 2008.

* cited by examiner

*Primary Examiner* — David Isabella
*Assistant Examiner* — Suba Ganesan
(74) *Attorney, Agent, or Firm* — Reichel IP LLP; Mark C. Reichel; Kevin R. Erdman

(57) ABSTRACT

Systems and methods for remodeling the annulus of a valve are disclosed. At least some embodiments disclosed herein are useful for resizing the mitral valve annulus in a safe and effective way. Such remodeling can be used to treat mitral valve regurgitation. At least some of the disclosed embodiments adjust the size of a valve annulus using magnetic forces. Other embodiments may include mechanisms for the manual adjustment of the annulus.

27 Claims, 18 Drawing Sheets

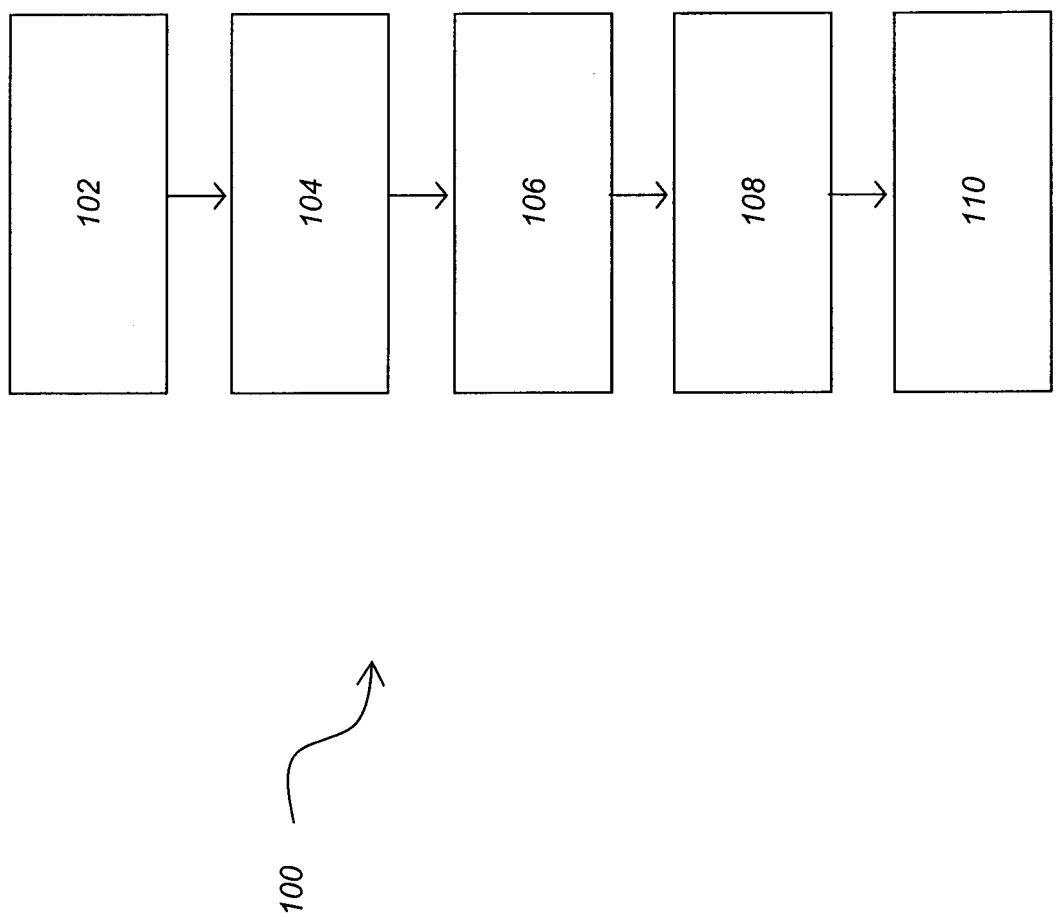

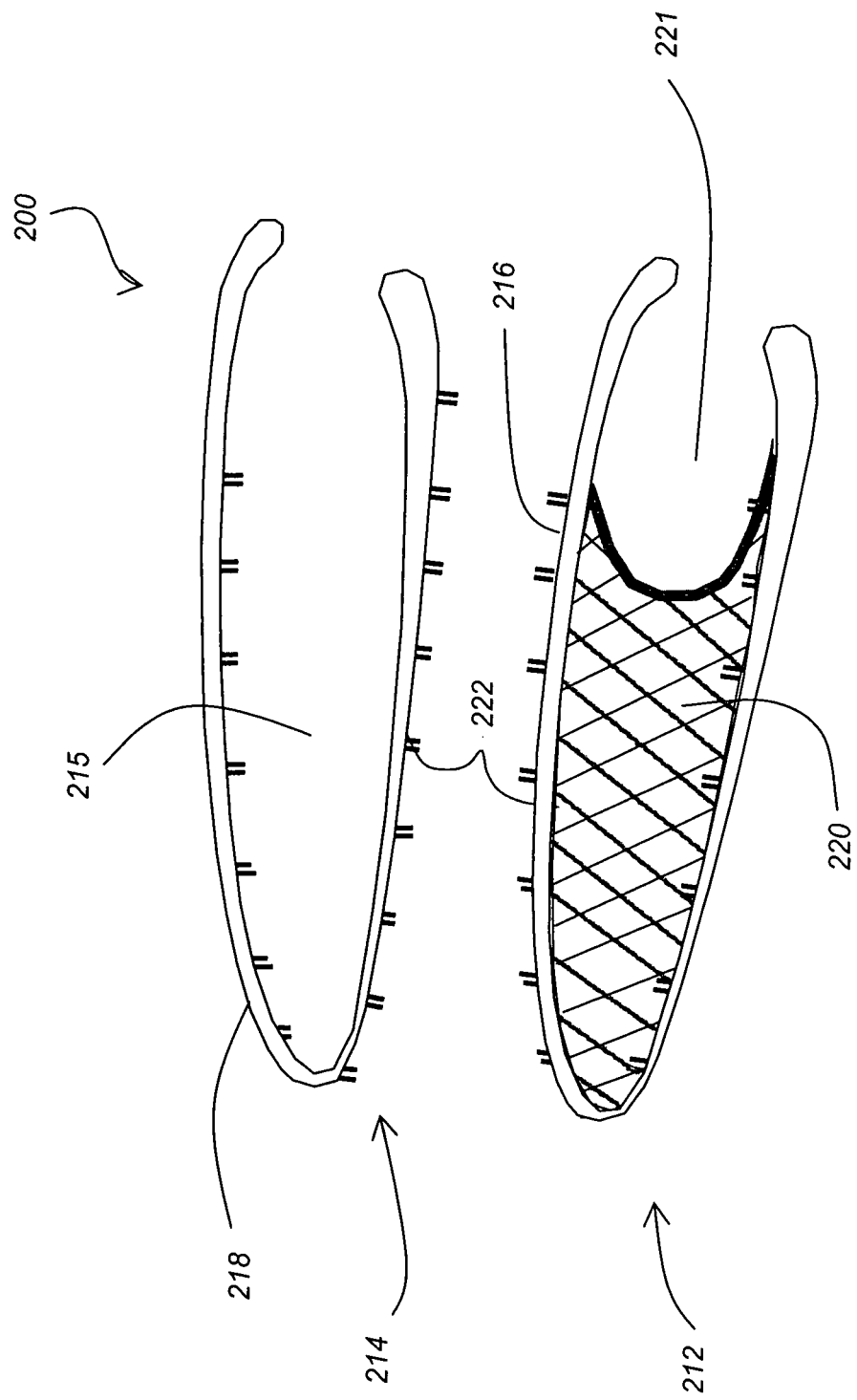

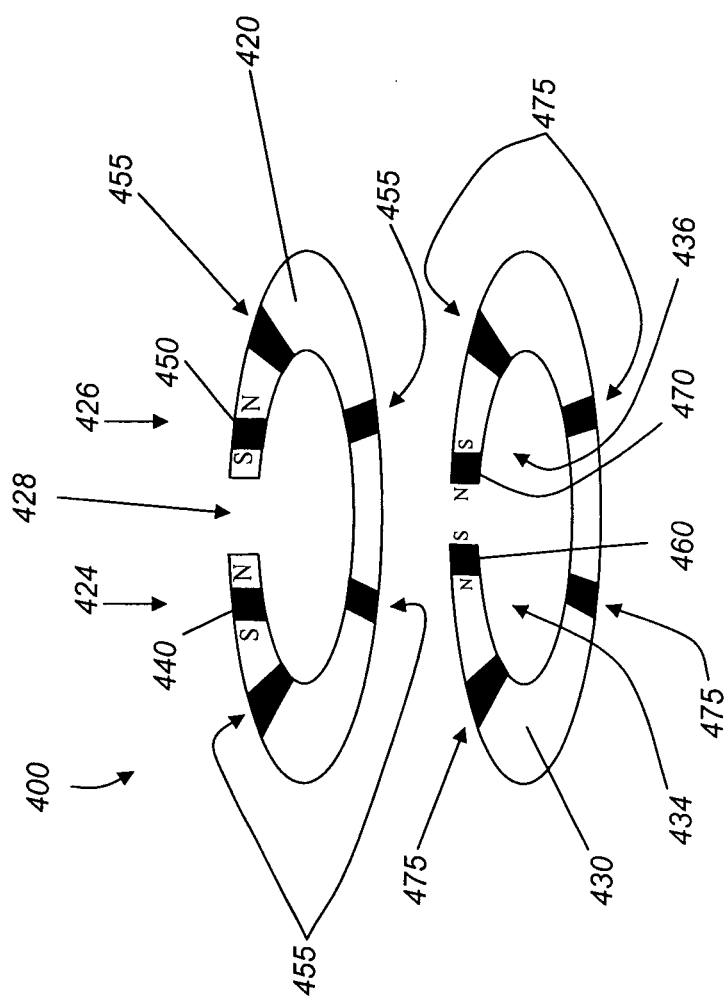

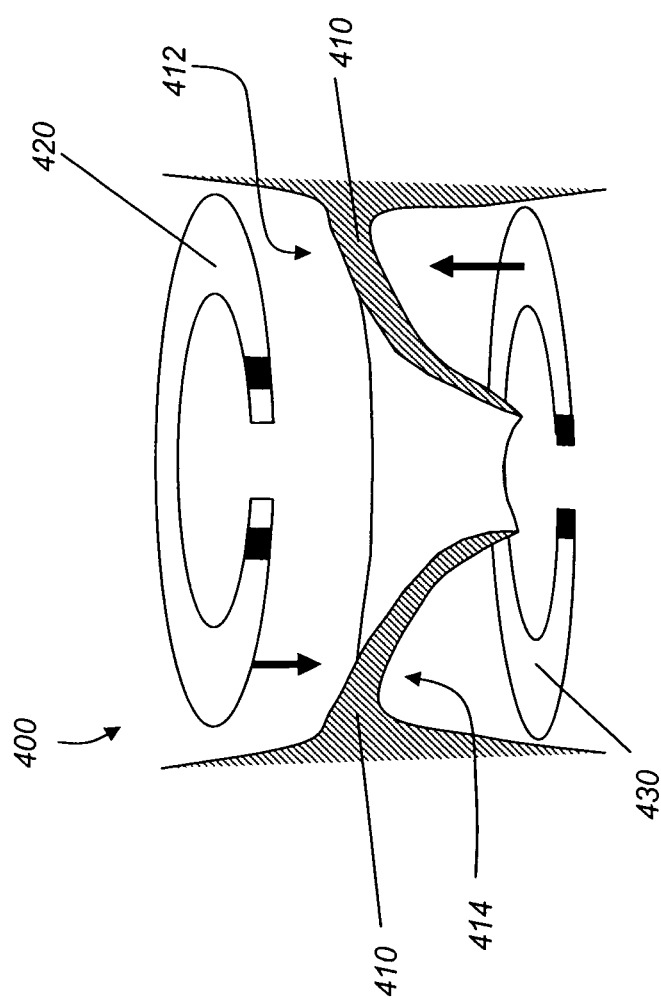

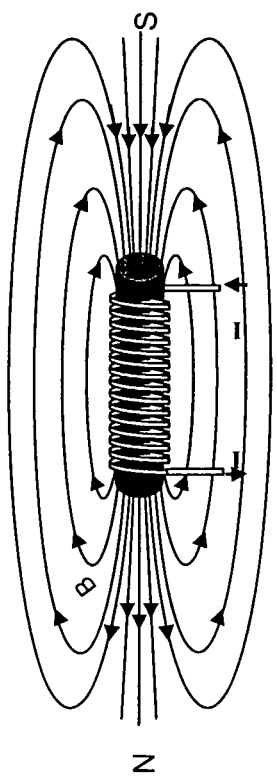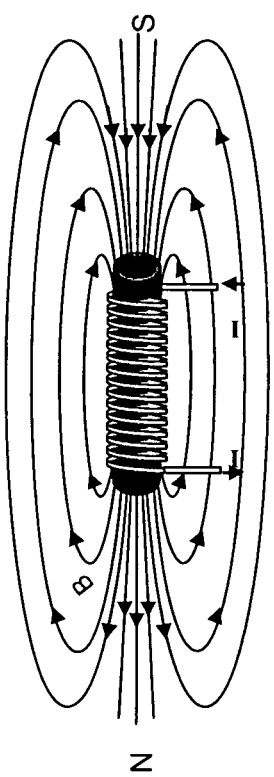
Fig. 10

SYSTEMS AND METHODS FOR VALVE ANNULUS REMODELING

PRIORITY

The present application is related to, claims the priority benefit of, and is U.S. §371 national stage application of, International Patent Application Serial No. PCT/US2008/000840, filed Jan. 23, 2008, which (a) is related to, and claims the priority benefit of, and is a continuation-in-part of, International Patent Application Serial No. PCT/US2007/015267, filed Jun. 29, 2007, and (b) is related to, and claims the priority benefit of, U.S. Provisional Patent Application Ser. No. 60/881,836, filed Jan. 23, 2007. The contents of each of these applications are hereby incorporated by reference in their entirety into this disclosure.

BACKGROUND

The mitral valve connects the left atrium to the left ventricle and regulates blood flow between the two heart chambers. In the healthy heart, as the left atrium contracts, the mitral valve opens to let blood flow from the left atrium into the left ventricle. Then, when the left ventricle contracts to force blood throughout the body, the mitral valve closes to prevent blood from flowing back into the atrium. The valve has two flaps, or leaflets, that coapt to close the valve.

Mitral regurgitation, or mitral insufficiency, refers to the mitral valve's failure to close sufficiently, thereby allowing excessive leakage of blood from the ventricle back into the atrium. Ischemic mitral regurgitation is a type of mitral regurgitation caused by acute myocardial infarction and the left ventricular remodeling that can eventually result from the infarction. Millions of people throughout the world suffer from ischemic mitral regurgitation, including many who also suffer from chronic heart failure. In most patients with ischemic mitral regurgitation, the valve itself is structurally normal.

In end-stage heart failure patients, the mechanism of mitral regurgitation is multifactorial and is related to changes in left ventricular geometry, with a subsequent displacement of the subvalvular apparatus, annular dilatation, and restrictive leaflet motion, which ends in failure of the leaflet coaptation. Physiologically, ischemic mitral regurgitation in these patients will lead to left ventricular overload and decrease of stroke volume. This takes place at first in response to exercise and later can occur even at rest, which can activate systemic and local neurohormonal systems and cytokines that deteriorate cardiac loading conditions, promoting left ventricular remodeling and dysfunction. This may generate a vicious cycle where regurgitation produces more regurgitation.

Mitral valve repair may interrupt this cycle to safely improve clinical outcomes. The use of stringent restrictive rings (i.e., rings that are smaller than the measured size of the valve annulus) in valve annuloplasty may lead to better leaflet coaptation, which, in turn, decreases regurgitation and promotes reverse remodeling. The undersizing of the mitral annulus can lead to acute geometric changes of the base of the left ventricle, which may diminish left ventricular volume and wall stress.

BRIEF SUMMARY

Various embodiments disclosed herein relate to systems and methods for remodeling the annulus of a valve. At least some embodiments are useful for resizing the mitral valve annulus in a safe and effective way. Such remodeling can be used to treat mitral valve regurgitation. At least some of the disclosed embodiments adjust the size of a valve annulus using magnetic forces. Other embodiments may include mechanisms for the manual adjustment of the annulus.

At least some disclosed embodiments comprise a system for remodeling a valve annulus, comprising a first rod having a first end, a second end, a first ferromagnetic bar at the first end, a second ferromagnetic bar at a second end, and a third ferromagnetic bar between the first end and the second end; a second rod comprising a first end, a second end, and a first ferromagnetic bar; a first wire having a first end and a second end, a portion of the first wire being coiled around the first rod; and a second wire having a first end and a second end, a portion of the second wire being coiled around the second rod. The first wire and the first rod are capable of forming a first inductor, and the second wire and the second rod are capable of forming a second inductor. At least one of the first bar and the second bar may comprise neodymium, iron, and boron, a Heusler alloy, or $Fe_{80}B_{20}$.

The valve annulus to be remodeled may be a mitral valve annulus. However, at least some embodiments are useful with respect to other valves.

Certain embodiments further comprise a catheter for delivering at least one of the first rod and the second rod into a body lumen of a patient, wherein at least one of the first rod and the second rod are configured for delivery through the catheter. In at least some embodiments, the system further comprises a first power source operatively connected to a first wire. The first power source may comprise a first battery, which may be configured to supply a temporary electric current to the first wire.

In at least some embodiments, the system further comprises a second power source operatively connected to the second wire. The second power source may comprise a second battery, which may be configured to supply a temporary electric current to the second wire.

In at least some embodiments, the first rod is configured such that the first end of the first rod is positioned in proximity to the second end of the first rod and the first ferromagnetic bar of the first rod is capable of magnetic engagement with the second ferromagnetic bar of the first rod. The first rod may have a substantially circular shape.

In at least certain embodiments, the first ferromagnetic bar of the second rod is positioned at the first end of the second rod; the second rod further comprises a second ferromagnetic bar at the second end of the second rod and a third ferromagnetic bar positioned between the first and second ends of the second rod; and the second rod is configured such that the first end of the second rod is positioned in proximity to the second end of the second rod and the first ferromagnetic bar of the second rod is capable of magnetic engagement with the second ferromagnetic bar of the second rod. The second rod may have a substantially circular shape.

The third ferromagnetic bar of the first rod may be configured for magnetic engagement with the third ferromagnetic bar of the second rod.

In at least some embodiments, the first rod further comprises a plurality of ferromagnetic bars positioned between the first and second ends of the first rod; the second rod further comprises a plurality of ferromagnetic bars positioned between the first and second ends of the second rod; and the plurality of ferromagnetic bars of the first rod are configured for magnetic engagement with the plurality of ferromagnetic of the second rod.

In at least some other embodiments, a system for remodeling a valve annulus may comprise a first rod comprising a first end, a second end, and a first magnetic bar between the first end and the second end; a first finger and a second finger, the first and second fingers capable of forming a ring; an introducing catheter having a distal end, the distal end comprising a cinching mechanism; a first wire having a first end and a second end, the first wire being attached to the cinching mechanism such that the cinching mechanism causes tightening of the ring when the first wire is pulled; and a second wire having a first end and a second end, a portion of the second wire being coiled around the first rod; wherein the second wire and the first rod are capable of forming a first inductor.

Such embodiments may further comprise a power source operatively connected to the second wire and a delivery catheter configured for delivering the introducing catheter into a body lumen.

The first finger and second finger may comprise nitinol. In addition, the cinching mechanism may comprise a gear box and ratchet, a zipper, or a clicking mechanism.

Methods for remodeling the annulus of a valve are also disclosed herein. With respect to at least some disclosed embodiments, a method for remodeling a valve annulus in a heart may comprise introducing into the heart a first rod comprising a first end, a second end, a first ferromagnetic bar at the first end, a second ferromagnetic bar at the second end, and a third ferromagnetic bar between the first and second ends, the first rod having at least a portion of a first wire coiled around it, wherein the first wire is capable of operable connection to a power source; introducing into the heart a second rod comprising a first ferromagnetic bar; positioning the first rod onto a first face of the annulus; positioning the second rod onto a second face of the annulus; anchoring the first rod and the second rod to the annulus; and applying electrical current to the first wire to form a first inductor. In at least some embodiments, the valve annulus may be the mitral valve annulus.

In at least certain embodiments, the second rod further comprises a first end, a second end, a second ferromagnetic bar at the first end, and a third ferromagnetic bar at the second end, the second rod having at least a portion of a second wire coiled around it, wherein the second wire is capable of operable connection to a power source. In such situations, the method may further comprise the step of applying electrical current to the second wire to form a second inductor. The second wire may then be disconnected from the power source, which may comprise a battery. The embodiments may further comprise the step of restricting the circumference of the annulus, the step of disconnecting the first wire from the power source, or both steps.

In some embodiments, the step of anchoring the first rod and the second rod to the annulus comprises positioning the first rod and the second rod such that the third ferromagnetic bar of the first rod magnetically engages the first ferromagnetic bar of the second rod.

In at least some embodiments, the first rod has a substantially circular shape. The second rod may also have a substantially circular shape. At least one of the first bar and the second bar comprises a Heusler alloy.

In various disclosed embodiments, a method for remodeling a valve annulus in a heart may comprise introducing into the heart a rod having a first ferromagnetic bar, the rod having at least a portion of a first wire coiled around the rod, the first wire capable of operative attachment to a power source; positioning the first rod onto a first face of the annulus; applying electric current to the first wire; extending into the heart an introducing catheter having a cinching mechanism attached to a distal end of the introducing catheter; introducing into the heart through the introducing catheter a first finger and a second finger, wherein the first finger is attached to the cinching mechanism; positioning the first finger and the second finger on the second face of the annulus to form a ring; and constricting the circumference of the ring. The first finger and second finger may comprise nitinol.

The rod may further comprise a first end, a second end, and a second ferromagnetic bar positioned between the first and second ends. The cinching mechanism may comprise a gear box and ratchet, a zipper, or a clicking mechanism.

BRIEF DESCRIPTION OF THE DRAWINGS

FIG. 4 shows a flow chart of an embodiment of a method for using the occlusion device of FIGS. 1 and 2 to occlude an opening in a tissue, as disclosed herein;

FIG. 5 shows a schematic view of another embodiment of an occlusion device for occluding an opening in a tissue, as disclosed herein;

FIG. 9A shows a perspective view of an embodiment of a system for remodeling a valve annulus, as disclosed herein;

FIG. 9C shows the embodiment of a system for remodeling a valve annulus shown in FIG. 9A, as being placed near a valve annulus;

FIG. 10 shows a depiction of two magnetic fields created using straight ferromagnetic bars, as disclosed herein;

DETAILED DESCRIPTION

It will be appreciated by those of skill in the art that the following detailed description of the disclosed embodiments is merely exemplary in nature and is not intended to limit the scope of the appended claims.

The disclosed embodiments include systems and methods for remodeling the annulus of a valve. For example, at least some embodiments disclosed herein are useful for resizing the mitral valve annulus in a safe and effective way. Such remodeling can be used to treat mitral valve regurgitation.

Figure 1:
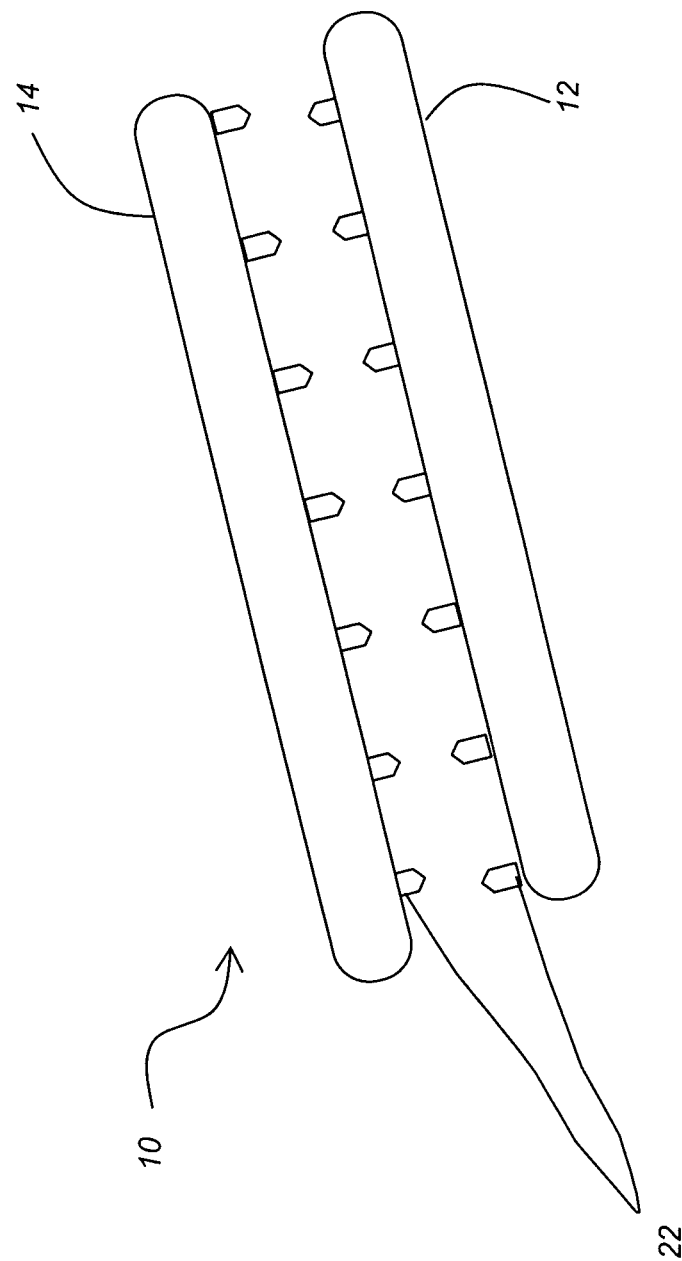
FIG. 1 shows a side view of an embodiment of an occlusion device for reducing the size of an opening, as disclosed herein.

FIG. 1 shows a schematic view of one embodiment of an occlusion device 10 for reducing the size of an opening. In this embodiment, the occlusion device 10 is comprised of a first magnetic component 12 and a second magnetic component 14. The first magnetic component 12 is comprised of a first shape and the second magnetic component 14 comprises a second shape that matches at least a portion of the first shape of the first magnetic component 12. The first magnetic component 12 and the second magnetic component 14 are each comprised of any ferromagnetic material known in the art so long as the material is capable of magnetically engaging through a tissue. In addition, the first and second magnetic components 12, 14 may be flexible, semi-flexible, or articulated.

In the embodiment shown in FIG. 1, the first and second magnetic components 12, 14 each comprise a straight bar. It will be recognized that while the first and second magnetic components 12, 14 of FIG. 1 are shown as straight bars, any configuration may be used so long as the first and second components 12, 14 are capable of being inserted into a body cavity laparoscopically and are capable of magnetically engaging with each other through a tissue (i.e., the sandwich effect).

The first magnetic component 12 and the second magnetic component 14 are polarized such that the first and second magnetic components 12, 14 are biased towards each other. Due to the configuration of the second magnetic component 14 and the bias between the first magnetic component 12 and the second magnetic component 14, the first and second magnetic components 12, 14 are capable of magnetically engaging. When the first and second magnetic components 12, 14 magnetically engage, the two components form a single unit that is secured to any tissue disposed between the two magnetic components 12, 14.

In one embodiment, the occlusion device 10 may further comprise a plurality of barbs 22. In this embodiment, the barbs 22 extend from both the first magnetic component 12 and the second magnetic component 14 such that the barbs 22 mechanically engage the opposite magnetic component when the first and second magnetic components 12, 14 are in close proximity and magnetically engaged. In this manner, the plurality of barbs 22 function to reinforce the engagement between the first magnetic component 12 and the second magnetic component 14 when the first and second magnetic components 12, 14 are in close proximity.

The plurality of barbs 22 may be sharp, pointed, or dull and comprise any material known in the art that does not interfere with the magnetic engagement between the first magnetic component 12 and the second magnetic component 14. In an additional embodiment, each of the barbs 22 protruding from the first and second magnetic components 12, 14 has a corresponding indentation (not shown) located on the opposite magnetic component. Accordingly, when the first magnetic component 12 and the second magnetic component 14 mechanically engage, each of the plurality of barbs 22 is received by its corresponding indentation in the opposite magnetic component.

Figure 2:
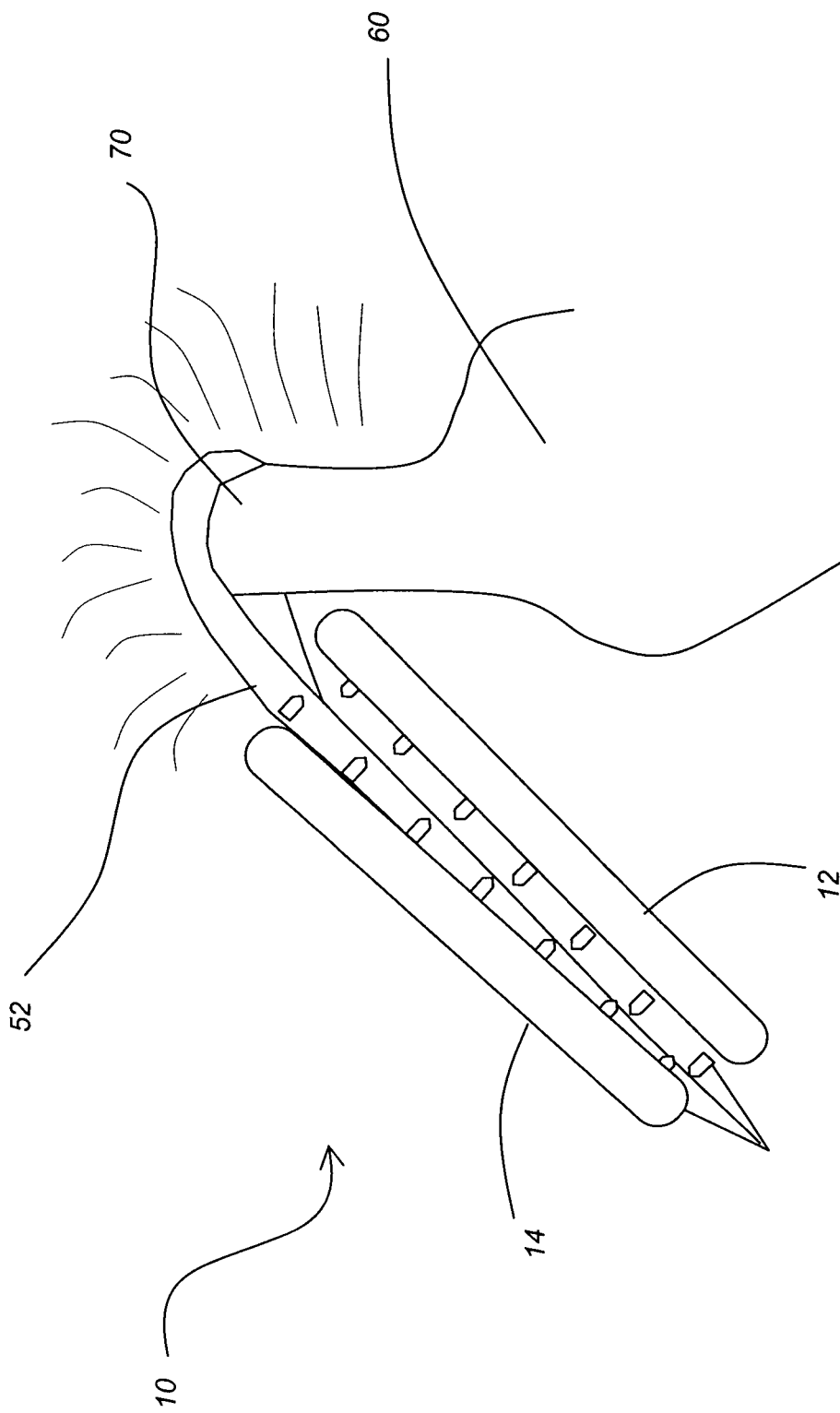
FIG. 2 shows the occlusion device shown in FIG. 1 positioned proximate to the site of a hiatal hernia.

FIG. 2 shows a bottom view of the occlusion device 10 implanted for use to treat and/or prevent a hiatal hernia. In this embodiment, the occlusion device 10 is employed as a "Non-Tension Free" device because the placement of the occlusion device 10 relative to the diaphragm 52 creates tension on the crus of the diaphragm 52. The esophagus 70 passes through a "hiatus," or opening, in the diaphragm wall 52 before reaching the stomach 60. As a consequence of either physical debilities attending acid reflux disease, obesity, or other medical ailments, the esophageal hiatus may become enlarged and a hiatal hernia may develop. A hiatal hernia is a protrusion of the stomach upward into the mediastinal cavity through the esophageal hiatus of the diaphragm 52. By applying the occlusion device 10 to the diaphragm 52 adjacent to the esophageal hiatus, the condition can be corrected and/or avoided altogether.

In FIG. 2, the occlusion device 10 is shown coupled with the diaphragmatic wall 52 in a location adjacent to both the stomach 60 and the esophagus 70. In this embodiment, the first and second magnetic components 12, 14 each comprise a straight bar configuration. In application, both the first magnetic component 12 and the second magnetic component 14 are positioned adjacent to the inferior wall of the diaphragm 52 or, alternatively, the superior wall of the diaphragm 52. As shown in FIG. 2, the occlusion device 10 is positioned adjacent to the inferior wall of the diaphragm 52 in an anterior placement.

When the first magnetic component 12 and the second magnetic component 14 are positioned in close proximity to one another, the first and second magnetic components 12, 14 are biased towards each other. To treat and/or prevent a hiatal hernia, the first and second magnetic components 12, 14 are positioned adjacent to the edges of the enlarged esophageal hiatus and allowed to magnetically engage one another such that a portion of the diaphragm wall 52 is disposed and compressed therebetween. The compression resulting from the magnetic engagement of the occlusion device 10 compresses the edges of the esophageal hiatus together and thereby reduces the size of the diaphragmatic opening. Depending on the specific placement of the occlusion device 10, the occlusion device 10 may be operable to reduce the size of the esophageal hiatus so that the hiatus is only approximately the diameter of the esophagus 70 traversing therethrough. By removing the additional space from the hiatus, the placement and structure of the occlusion device 10 prevent the stomach 60 from protruding through the diaphragm wall 52 and into the mediastinal cavity via the esophageal hiatus.

In an alternative embodiment of the occlusion device 10, the occlusion device 10 may comprise a single magnetic component (not shown). In this embodiment, at least a portion of the magnetic component is flexible or semi-flexible, such that at least a section of the magnetic component is capable of folding. The magnetic component of this embodiment comprises a first end and a second end. In operation, the portion of the magnetic component that is flexible or semi-flexible folds, such that the first end and the second end can magnetically engage each other. In this manner, the single magnetic component can function as a clamp. For example, the magnetic component of this embodiment is operable to clamp a portion of the edge of an enlarged esophageal hiatus (in the manner illustrated in FIG. 2), thereby resulting in an esophageal hiatus with a smaller diameter. In addition, the magnetic component of this embodiment may comprise a plurality of barbs 22 and corresponding indentations. As this embodiment of the occlusion device 10 only comprises one magnetic component, the barbs 22 and the corresponding indentations are necessarily both located on the same component of the occlusion device 10.

The magnetic force between the first and second magnetic components 12, 14 of the occlusion device 10 reduces the risk that the occlusion device 10 will become displaced or dislodged over time. In addition, in the embodiments where the occlusion device 10 further comprises a plurality of barbs 22, the plurality of barbs 22 further secure the occlusion device 10 to the diaphragm wall 52, and/or the first magnetic component 12 to the second magnetic component 14, thereby further securing the occlusion device 10 to the diaphragm wall 52 and preventing the occlusion device 10 from shifting or becoming dislodged. For example, depending on the configuration of the barbs 22, the barbs 22 may form a wave-like pattern in the diaphragm tissue 52 and increase the amount of force required to dislodge the occlusion device 10 from the diaphragm 52. Alternatively, the barbs 22 may be configured as sharp points such that the barbs 22 puncture the diaphragmatic tissue 52 and thus function similarly to sutures or staples by securing the occlusion device 10 to the diaphragm 52. Accordingly, the barbs 22 can provide further resistance and prevent the occlusion device 10 from shifting relative to the esophagus 70 or the diaphragm 52.

Figure 3B:
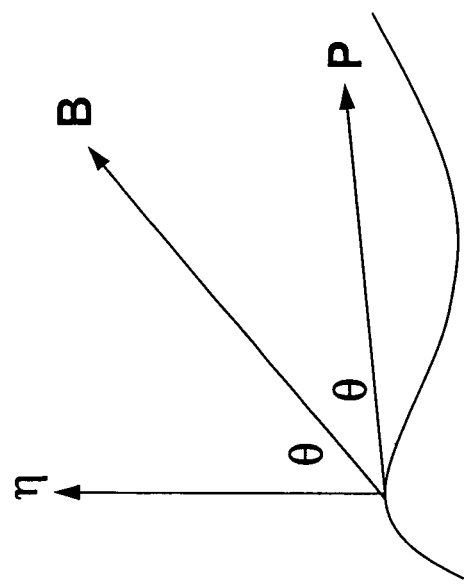
FIGS. 3A and 3B show graphical representations of the magnetostatic forces involved in the calculation of the field strength between the two parallel plates of the occlusion device of FIGS. 1 and 2.
Figure 3A:
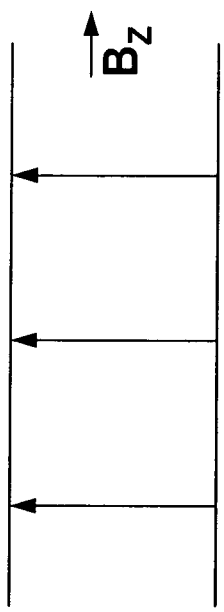

A user of the occlusion device 10 (e.g., a clinician) may also select specific permanent magnets to comprise the first and second magnetic components 12, 14 such that the first and second magnetic components 12, 14 exert an optimal amount of magnetostatic force to promote the stabilization of the occlusion device 10. For the theoretical application of the occlusion device 10 in the stomach of obese persons, an example calculation is provided below. In light of the two parallel plates shown in FIG. 3A, the Maxwell's stress tensor is written as follows:

$$T_{ij} = \frac{1}{\mu}\left[B_i B_j - \frac{1}{2}B^2 \delta_{ij}\right] \quad [1]$$

Since only $\vec{b}_z$ exists in this application, the Maxwell's stress tensor is written as:

$$T_{ij} = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \quad [2]$$

The stress tensor vector which is normal to the surface in two-dimensional coordinates has the form:

$$P = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \begin{pmatrix} 0 \\ 0 \\ n_z \end{pmatrix} = \frac{|B_z|^2}{2\mu} \quad [3]$$

where, if $|B_z|=0.5$ T, the pressure is calculated as follows:

$$P = \frac{|B_z|^2}{2\mu} = \frac{0.5^2}{8\pi \times 10^{-7}} = 99.47 \text{ (kPa)} \quad [4]$$

If it is assumed that the angle between the magnetic field B and normal direction of the magnetic plate is taken as 15°, and area=$[2\pi \times (1.0 \times 10^{-2})] \times (0.5 \times 10^{-2})$m² (illustrated in FIG. 3B), the force is calculated as follows:

$$F = P \times \sin 30° \times \text{area} = 99.47 \times 0.5 \times \pi \times 0.1 = 15.62 \text{(Newton)} \quad [5]$$

The force determined by Equation 5 represents the tangential force required to oppose or resist movement or migration of the occlusion device 10. Accordingly, the occlusion device 10 can be designed to yield a required force. The area of the occlusion device 10 may also be appropriately designed to spread out the force in order to minimize the compression of the tissue. Other forces may be similarly determined for different geometries and areas under consideration.

FIG. 4 shows a flow chart of a method 100 for reducing the size of an esophageal hiatus by employing the occlusion device 10. For ease of understanding, the steps of the related methods described herein will be discussed relative to the components of the occlusion device 10 shown in FIGS. 1 and 2, but it will be appreciated by one skilled in the art that any such device can be used to perform these methods, so long as the device is capable of magnetically engaging a magnetic composition through a piece of tissue, such that the engagement is secure.

At step 102, the first and second magnetic components 12, 14 are inserted laparoscopically into the patient's body. In this embodiment and the embodiment where the occlusion device 10 comprises a single flexible magnetic component, the magnetic component(s) may be inserted through a catheter into the patient's abdominal cavity. At step 104, the first and second magnetic components 12, 14 are positioned adjacent and parallel to the inferior surface of the diaphragm 52. Downward tension is applied to the edges of the enlarged portion of the esophageal hiatus at step 106 and the edges are folded down into the abdominal cavity. In this manner, the superior surfaces of the diaphragm 52 on each side of the esophageal hiatus are positioned adjacent to each other and are in physical communication. In an alternative embodiment of the method 100, the occlusion device is positioned adjacent and parallel to the superior surface of the diaphragm 52 at step 104. In this embodiment, at step 106 upward tension is applied to the edges of the enlarged portion of the esophageal hiatus. Accordingly, the edges are folded up into the thoracic cavity.

In both embodiments of the method 100, at step 108 the first magnetic component 12 is positioned on one side of the pinched edges of the hiatus, and the second magnetic component 14 is positioned on the opposite side of the pinched edges of the hiatus. The first and second magnetic components 12, 14 are then allowed to magnetically engage at step 110, such that the edges of the hiatus are compressed therebetween. In securing the edges of the hiatus in such a manner, the occlusion device 10 decreases the size of, thereby occludes, the esophageal opening.

FIG. 5 shows a schematic view of an alternative embodiment of the occlusion device 10. The only difference between the occlusion device 10 and the occlusion device 200 is that the magnetic components of the occlusion device 200 may each define an interior. In the embodiment shown in FIG. 5, the occlusion device 200 is comprised of a first magnetic component 212 and a second magnetic component 214. The first magnetic component 212 comprises a first magnetic shape 216 that defines an interior area 215. The first magnetic component 212 may be comprised of any ferromagnet known in the art that is capable of magnetically engaging the second magnetic component 214 through a tissue and may be flexible, semi-flexible, or articulated.

The first magnetic component 212 further has a section of mesh 220 disposed across a portion of the interior 215 defined by the first magnetic shape 216. The mesh 220 may be comprised of any non-reabsorbable material, whether synthetic or biological, that is known in the art. Examples of such non-reabsorbable materials include, but are not limited to, polytetrafluoroethylene, polyurethane, or pericardium. Because the mesh 220 is not disposed across the totality of the interior 215 of the first magnetic component 212, an opening 221 is defined. The opening 221 may comprise any size or configuration necessary for the desired application of the occlusion device 200. The first magnetic shape 216 may be configured in any shape so long as the first magnetic shape 216 defines the interior 215 and at least one end of the first magnetic shape 216 is open. Merely by way of example, and without any intended limitation, the first magnetic shape 216 may be configured as in a rectangular shape, C-shape, U-shape, or V-shape.

The second magnetic component 214 comprises a second magnetic shape 218 that matches at least a portion of the first magnetic shape 216 of the first magnetic component 212. As shown in FIG. 5, the second magnetic shape 218 may comprise a U-shape. While the embodiment of the second magnetic shape 218 shown in FIG. 5 defines the interior area 215, it will be recognized that the second magnetic shape 218 of the second magnetic component 214 need not define the interior area 215 so long as the second magnetic shape 218 matches at least a portion of the first magnetic shape 216. The second magnetic component 214 may be comprised of any ferromagnet known in the art that is capable of magnetically engaging the first magnetic component 212 through a tissue. In addition, the second magnetic component 214 may be flexible, semi-flexible, or articulated.

In the embodiment shown in FIG. 5, the first magnetic component 212 and the second magnetic component 214 comprise permanent magnets having U-shape configurations. The first magnetic component 212 comprises the mesh 220 that extends radially inward from the first magnetic shape 216. In this embodiment, the opening 221 is disposed proximate to the open end of the first magnetic component 212. In an alternative embodiment, the first magnetic component 212 and the second magnetic component 214 both comprise the mesh 220 extending across the interior 215 such that a double layer of mesh 220 is provided when the first and second magnetic components 212, 213 magnetically engage.

The first magnetic component 212 and the second magnetic component 214 are polarized such that they are biased towards each another. Due to the matching configuration and the bias between the first magnetic component 212 and the second magnetic component 214, the first and second magnetic components 212, 214 are capable of magnetically engaging. When the first and second magnetic components 212, 214 magnetically engage, a single unit is formed and secured to any tissue disposed between the two magnetic components 212, 214.

Similar to the occlusion device 10, in one embodiment of the occlusion device 200, the first and second magnetic components 212, 214 further comprise a plurality of barbs 222. In this embodiment, the plurality of barbs 222 extend from both the first and second magnetic components 212, 214 such that the barbs 222 mechanically engage the opposite magnetic component when the first magnetic component 212 and the second magnetic component 214 are in close proximity and magnetically engaged. In this manner, the plurality of barbs 222 function to reinforce the engagement between the first magnetic component 212 and the second magnetic component 214.

Similar to the barbs 22 described in conjunction with one embodiment of the occlusion device 10, the barbs 222 may be sharp, pointed, or dull and comprise any material known in the art that does not interfere with the magnetic engagement between the first magnetic component 212 and the second magnetic component 214. In one embodiment, each of the barbs 222 protruding from the first and second magnetic components 212, 214 has a corresponding indentation (not shown) located on the opposite magnetic component. Accordingly, when the first magnetic component 212 and the second magnetic component 214 mechanically engage, each of the plurality of barbs 222 is received by its corresponding indention in the opposite magnetic component. In this manner, the plurality of barbs 222 and the corresponding indentations function to secure the first magnetic component 212 to the second magnetic component 214.

Figure 6:
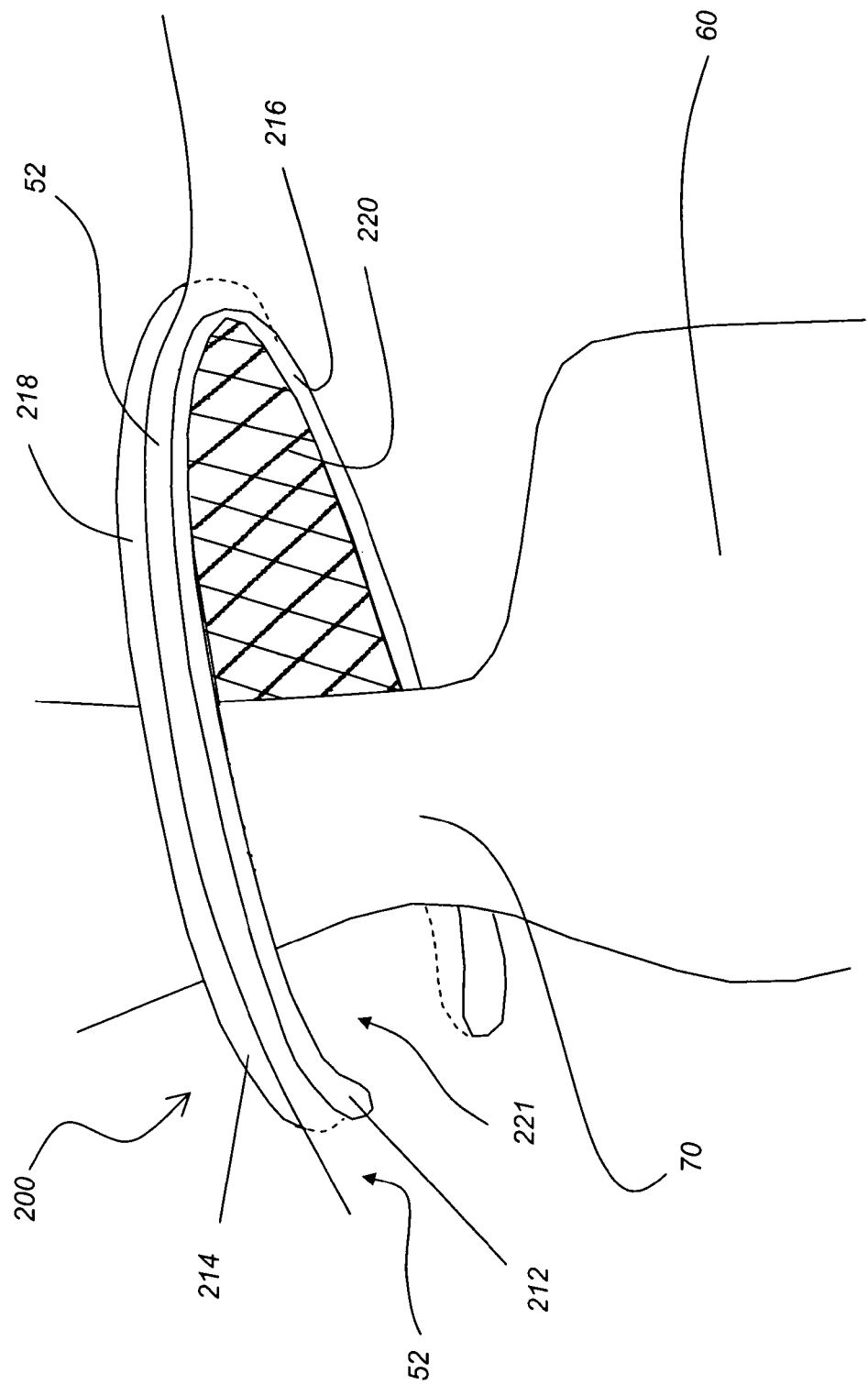
FIG. 6 shows a bottom view of the occlusion device of FIG. 5 positioned around the site of a hiatal hernia in an anterior placement.
Figure 7:
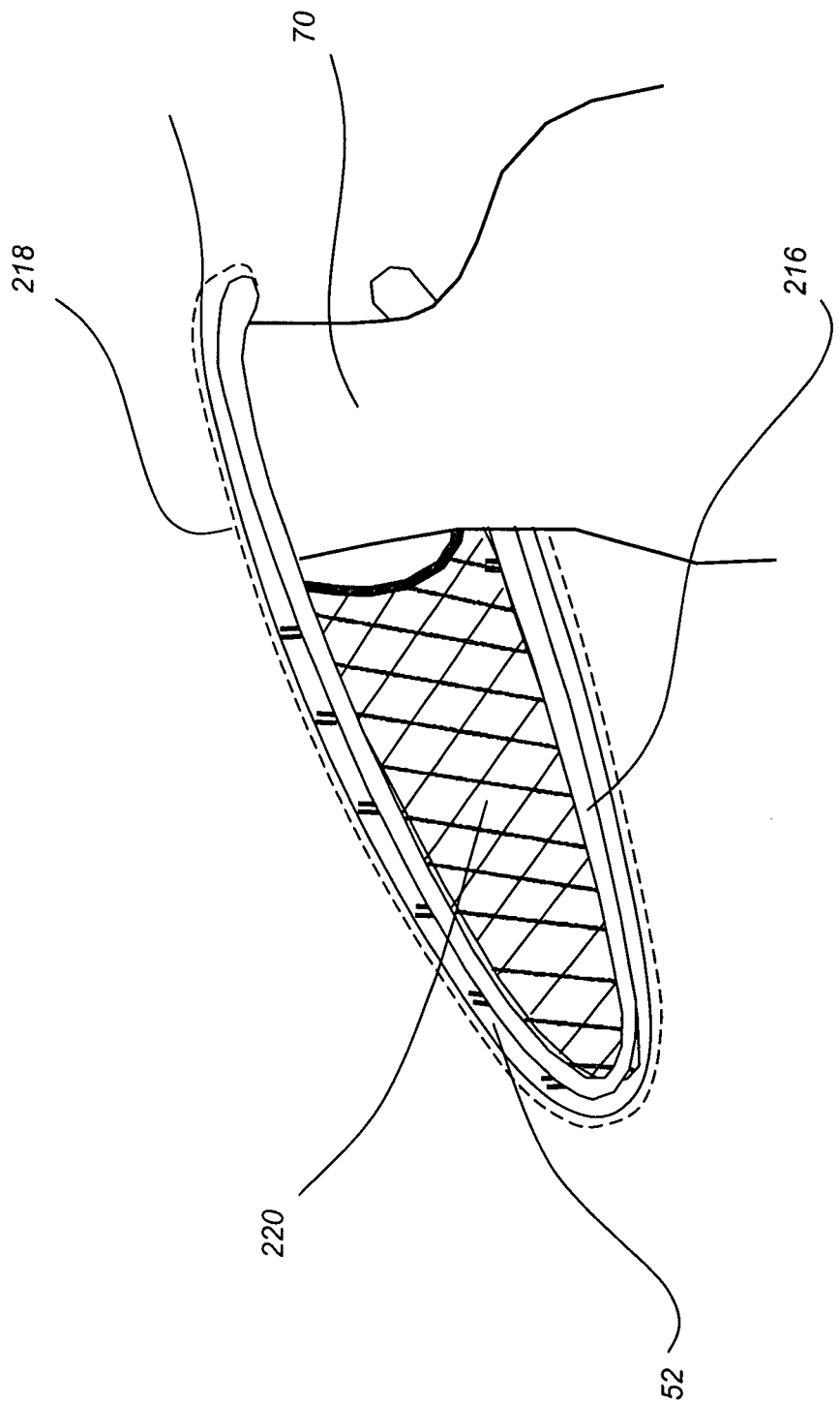
FIG. 7 shows the occlusion device shown in FIG. 5 positioned around the site of a hiatal hernia in a posterior placement.

Now referring to FIGS. 6 and 7, FIGS. 6 and 7 depict diagrammatic, bottom views of one embodiment of the occlusion device 200 implanted for use to treat and/or prevent a hiatal hernia. In this embodiment, the occlusion device 200 is employed as a "Tension-Free" device because it avoids mechanical mesh fixation. By avoiding mechanical mesh fixation, the occlusion device 200 prevents injuries to the vital structure surrounding the esophageal hiatus and provides for ease in insertion and removal from a patient. Additionally, employing a soft biologic or synthetic mesh avoids the formation of a visceral adhesion, local fibrosis (dysphagia), or esophageal erosion.

In FIG. 6, the occlusion device 200 is shown coupled with the diaphragmatic wall 52 and the esophagus 70 in a location adjacent to the stomach 60. In this embodiment, the first and second magnetic components 212, 214 each comprise a C-shaped configuration and have an open end and a closed end. In addition, the opening 221 of the first magnetic component 212 comprises a diameter that closely approximates the diameter of the esophagus 70 at the gastroesophageal junction.

In application, the first magnetic component 212 is positioned adjacent to the inferior wall of the diaphragm 52 with the open end of the first magnetic component 212 positioned around the esophagus 70. The second magnetic component 214 is positioned adjacent to the superior wall of the diaphragm 52 such that the second magnetic component 214 is positioned around the esophagus 70. Due to the size of the opening 221, only the esophagus 70 is able to fit therethrough. The occlusion device 200 may be applied to the diaphragm 52 in a posterior or anterior placement, depending on the site of the herniation. While the occlusion device 200 is shown in the anterior placement in FIG. 6, FIG. 7 illustrates the occlusion device 200 as applied to the diaphragm 52 in the posterior placement.

Due to the close proximity of the first magnetic component 212 and the second magnetic component 214, the first and second magnetic components 212, 214 magnetically engage through the diaphragm wall 52, compressing the diaphragm wall 52 therebetween. In one embodiment, the mesh 220 is coupled with the inferior wall of the diaphragm 52 due to the magnetic forces exerted by the first and second magnetic components 212, 214. In this embodiment, because the mesh 220 is coupled with the diaphragm 52, after implantation, diaphragmatic tissue may grow into the mesh 220. This tissue growth further secures the occlusion device 200 to the diaphragm 52.

In the embodiments shown in FIGS. 6 and 7, the size of the opening 221 of the first magnetic component 212 is equivalent to the diameter of the esophagus 70; therefore the mesh 220 occludes any portion of an esophageal hiatus that the esophagus 70 does not occupy. By covering any unnecessary space of the esophageal hiatus and/or any weakened diaphragmatic tissue, the placement and structure of the occlusion device 200 prevent the stomach 60 from protruding through the diaphragm wall 52 and into the mediastinal cavity via the esophageal hiatus.

The structure and placement of the occlusion device 200 further reduces the risk that the occlusion device 200 will become displaced or dislodged over time. The magnetic force between the first magnetic component 212 and the second magnetic component 214, the diaphragmatic tissue growth into the mesh 220, and the first and second magnetic components 212, 214 both partially surrounding the esophagus 70 all assist in anchoring the occlusion device 200 in its desired position. In the embodiment wherein the occlusion device 200 further comprises a plurality of barbs 222, the plurality of barbs 222 further secure the occlusion device 200 to the diaphragm wall 52 and prevent the occlusion device 200 from shifting or becoming dislodged.

Depending on the configuration of the barbs 222, the barbs 222 may form a wave-like pattern in the diaphragm tissue 52 and increase the amount of force required to dislodge the occlusion device 200 from the diaphragm 52. In an additional embodiment, the barbs 222 are configured as sharp points such that the barbs 222 puncture the diaphragmatic tissue, thus functioning similarly to sutures or staples by securing the occlusion device 200 to the diaphragm 52. Even though the barbs 222 may puncture the diaphragmatic tissue, the barbs 222 will not produce the complications seen with the sutures and staples used in the prior art because the barbs 222 produce less ischemic effect in the diaphragmatic muscles. In these ways, the barbs 222 can provide further resistance and prevent the occlusion device 200 from shifting relative to the esophagus 70 or the diaphragm 52.

Figure 8:
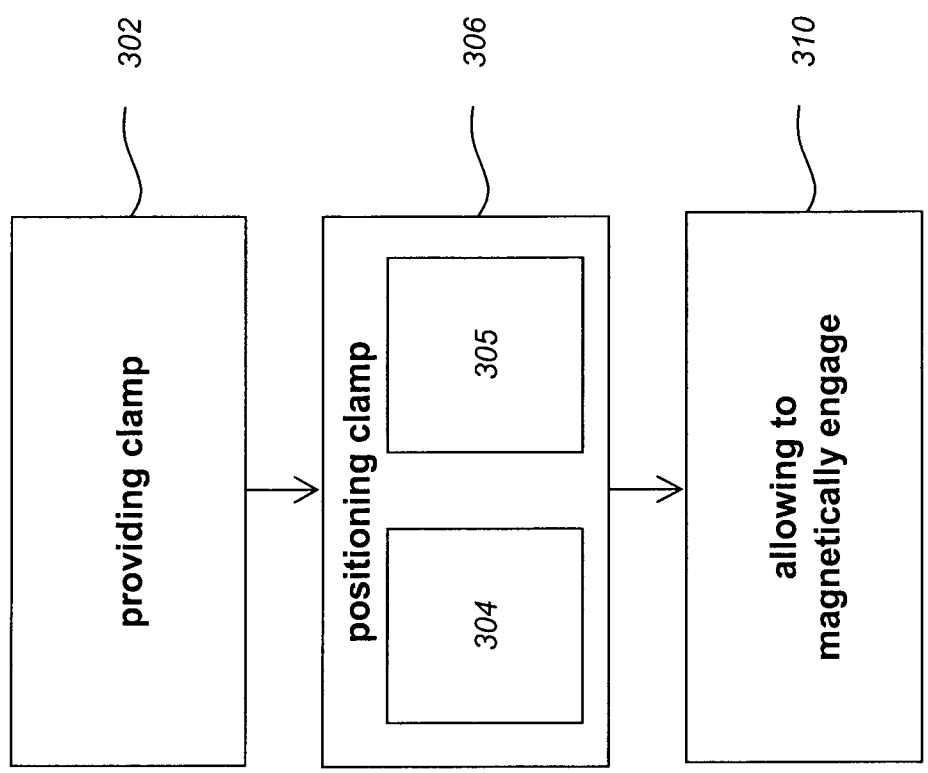
FIG. 8 shows a flow chart of an embodiment of a method for using the occlusion device of FIG. 5 to cover an opening in a tissue, as disclosed herein.

FIG. 8 shows a flow chart of one embodiment of a method 300 for occluding a tissue opening. For ease of understanding, the steps of the related methods described herein will be discussed relative to the components of the occlusion device 200 shown in FIGS. 5-7, but it will be appreciated by one skilled in the art that any such device can be used to perform these methods, so long as the device is capable of magnetically engaging a magnetic composition through a piece of tissue such that the engagement is secure.

Generally, a clinician can utilize the occlusion device 200 shown in FIGS. 5-7 to occlude a tissue opening, and specifically to treat and/or prevent a hiatal hernia. As shown in FIG. 8, step 302 comprises providing the occlusion device 200, or a similar device capable of occluding an opening in a tissue. At step 306, the occlusion device 200 is adhered to the diaphragm 52 in such a manner that at least a portion of the mesh 220 occludes a portion of the hiatus. In one embodiment of the method 300, step 306 may comprise two independent steps. Specifically, step 304 comprises positioning the first magnetic component 212 of the occlusion device 200 adjacent to the inferior portion of the diaphragm 52 (i.e., within the abdominal cavity) and around the esophagus 70. Step 305 comprises positioning the second magnetic component 214 adjacent to the superior portion of the diaphragm (i.e., within the chest cavity) and inserting the esophagus into the opening 221. Due to the bias between the first and second magnetic components 212, 214, aligning the two components 212, 214 with one another on opposite sides of the diaphragm 52 is an uncomplicated process, even when the occlusion device 200 is being implanted through laparoscopic technique. When the first and second magnetic components 212, 214 are substantially aligned, the mesh 220 effectively occludes the excess space in the esophageal hiatus, thus allowing only the esophagus 70 to traverse the diaphragm wall 52.

Once the components of the occlusion device 200 are positioned on opposite sides of the diaphragm 52 and properly aligned with the esophagus 70 and esophageal hiatus, at step 310 the first magnetic component 212 and the second magnetic component 214 are allowed to magnetically engage. Because of the placement of the components relative to the diaphragm 52 and the esophagus 70, the diaphragmatic tissue 52 is compressed between the first magnetic component 212 and the second magnetic component 214, and the esophagus 70 is restrained within the opening 221. The arrangement of the occlusion device 200 relative to the diaphragm 52 and the esophagus 70 anchors the occlusion device 200 to the diaphragm 52 and secures the mesh 220 such that the mesh 220 firmly blocks the hiatus. Due to the size, configuration, and simple implantation procedure of the occlusion device 200, the occlusion device 200 may be inserted into the body cavity laparoscopically, thereby reducing the number of incisions required and the amount of stress involved with administering treatment.

As disclosed herein, various embodiments of a system for remodeling a valve annulus may be used to, for example, remodel the mitral valve annulus. In at least some embodiments, the valve annulus may be adjusted automatically through a current delivered percutaneously. In at least some other embodiments, the valve annulus may be adjusted manually.

Figure 9B:
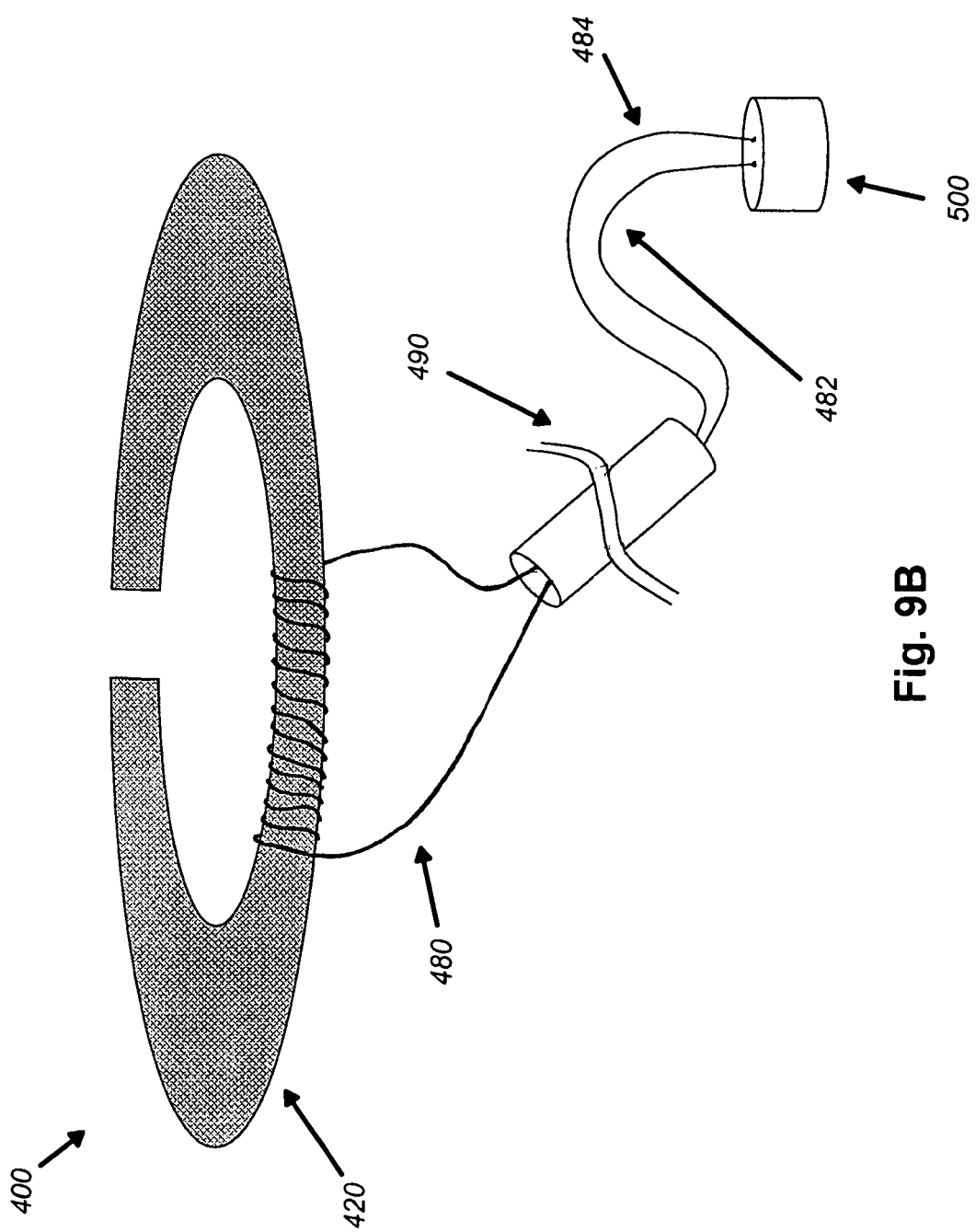
FIG. 9B shows another embodiment of the system for remodeling a valve annulus shown in FIG. 9A.

Referring now to FIGS. 9A, 9B, and 9C, there is shown a system 400 for remodeling a valve annulus 410 having a superior face 412 and an inferior face 414. System 400 comprises a first rod 420 and a second rod 430. First rod 420 comprises a first end 424 and a second end 426; second rod 430 comprises a first end 434 and a second end 436. On first rod 420, a first ferromagnetic bar 440 is positioned at first end 424, and a second ferromagnetic bar 450 is positioned at second end 426. As shown only in FIG. 9A, first rod 420 also has four additional ferromagnetic rods 455. Similarly, on second rod 430, a first ferromagnetic bar 460 is positioned at first end 434, and a second ferromagnetic bar 470 is positioned at second end 436. Second rod 430 also has four additional ferromagnetic rods 475 (shown only in FIG. 9A). However, in other embodiments, a second rod may not include ferromagnetic bars at its ends, so long as it has sufficient ferromagnetic bars for vertical engagement with the first rod. First rod 420 and second rod 430 may be made from any suitable metal, such as stainless steel, nitinol, or platinum.

As shown in FIGS. 9A and 9C, each of first rod 420 and second rod 430 has a substantially circular shape. However, other embodiments of rods may have other suitable shapes, such as an oval shape or a U-shape, so long as the rod properly fits the valve annulus and can effectively remodel the annulus to limit regurgitation. Regardless of the shape, at least some embodiments of rods have a gap, such as gap 428 of first rod 420 (see FIG. 9A). Such gaps permit adjustable sizing of the rods. Similarly, although system 400 comprises only two rods 420 and 430, other embodiments of systems may comprise more than two rods, which are placed around the annulus.

First rod 420 and second rod 430 are used to form a loop to resize the valve annulus to permit more effective closure of the valve. Such resizing may be accomplished using a horizontal magnetic force between the first and second ends of at least one of the bars. For example, first rod 420 is configured such that first end 424 of first rod 420 is positioned in proximity to second end 426 of first rod 420 and first ferromagnetic bar 440 of first rod 420 is capable of magnetic engagement with second ferromagnetic bar 450 of first rod 420. In other words, first ferromagnetic bar 440 of first rod 420 and second ferromagnetic bar 450 of first rod 420 should have opposite magnetic charges in closest proximity, so that each bar is magnetically attracted to the other. As shown in FIG. 9A, the northern pole of first ferromagnetic bar 440 of first rod 420 is facing the southern pole of second ferromagnetic bar 450 of first rod 420. Similarly, second rod 430 is configured such that first end 434 of second rod 430 is positioned in proximity to second end 436 of second rod 430 and first ferromagnetic bar 460 of second rod 430 is capable of magnetic engagement with second ferromagnetic bar 470 of second rod 430. For example, first ferromagnetic bar 460 of second rod 430 and second ferromagnetic bar 470 of second rod 430 should have opposite magnetic charges in closest proximity, so that each bar is magnetically attracted to the other.

In addition, first rod 420 and second rod 430 are magnetically attracted vertically because each has a number of ferromagnetic bars configured for vertical magnetic engagement. Referring again to FIG. 9A, ferromagnetic bars 455 are spread around rod 420, and ferromagnetic bars 475 are spread around rod 430. Each of ferromagnetic bars 455 of rod 420 is configured for magnetic engagement with one of ferromagnetic bars 475 of rod 430. Likewise, each ferromagnetic bar 475 of rod 420 is configured for magnetic engagement with one of ferromagnetic bars 455 of rod 420. For example, each of ferromagnetic bars 455 of rod 420 may have its southern pole facing downward toward rod 430, and each of ferromagnetic bars 475 of rod 430 may have its northern pole facing upward toward rod 420. Further, ferromagnetic bars 455 and ferromagnetic bars 475 are positioned on rod 420 and rod 430, respectively, to correspond such that one of ferromagnetic bars 455 will be in close proximity to one of ferromagnetic bars 475 when rods 420 and 430 are placed on opposing sides of annulus 410. Such close proximity enables ferromagnetic rods 455 and ferromagnetic rods 475 to magnetically engage. Thus, rods 420 and 430 are magnetically engaged and are therefore held together in proper alignment on valve annulus 410.

Each of ferromagnetic bar 440, 450, 455, 460, 470, and 475 may comprise a smooth, ferromagnetic filling bar and may be made from any suitable ferromagnetic material that is safe for implantation into a human body. For example, a ferromagnetic bar may comprise a polymer-bonded neodymium, iron, and boron magnet, a Heusler alloy, such as $Fe_{80}B_{20}$, or carbon-coated metal particles. Selecting appropriate magnetic materials is discussed in more detail herein.

Referring now to FIG. 9B, system 400 further comprises first wire 480, a portion of which is coiled around first rod 420. First wire 480 comprises a first end 482 and a second end 484, each of which extends through a first catheter 490 and is operatively attached to a power source 500 such that an electric current can flow through first wire 480. When current flows through first wire 480 over one of the ferromagnetic bars, a first inductor is formed. FIG. 10 shows a depiction of two magnetic fields created using straight ferromagnetic bars. In at least some embodiments, the power source is configured to supply a temporary electric current to the first wire. Thus, as is explained in more detail herein, the first inductor may be magnetized by supplying an electric current to the first wire and then removing the current.

Figure 11:
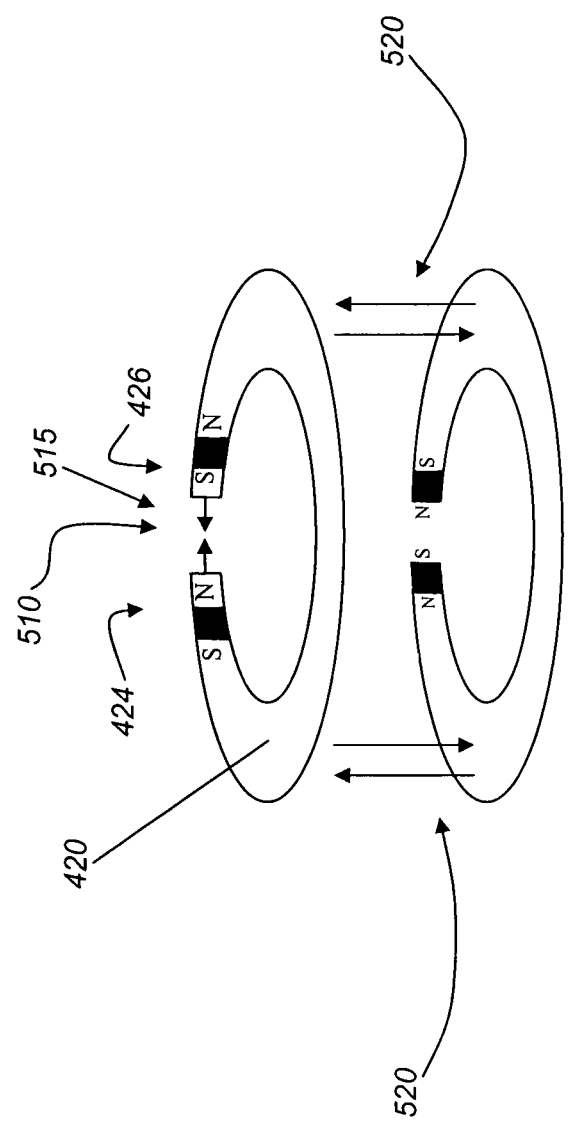
FIG. 11 shows the embodiment of a system for remodeling a valve annulus shown in FIG. 9A.

Although first wire 480 is shown in FIG. 9A as being coiled around a small portion of first rod 420, at least some other embodiments may have a first wire that is coiled around all or substantially all of the first rod. Indeed, a first wire may be coiled around as much of the first rod as is necessary to provide one or more inductors with sufficient to strength to work properly, as disclosed herein. The first wire is coiled along the bar in the horizontal direction to form the inductor (magnetic dipole) when an electric current is applied to the wire (see FIG. 10). In at least some embodiments, additional thin smooth ferromagnetic wires are coiled along the bar in the vertical direction to provide a force to attract the corresponding bar in the vertical direction (see FIG. 11).

Power source 500 is shown in FIG. 9B as a battery, but any suitable power source may be used. Power source 500 is located outside of the body, but at least some other embodiments may have a power source that is located within the body (e.g., placed subcutaneously).

System 400 further comprises a second wire (not shown), a portion of which is coiled around at least a portion of second rod 430. The second wire comprises a first end and a second end, each of which extends through catheter 490 and is operatively attached to a power source (not shown). In at least some embodiments, the second wire is attached to the same power source to which the first wire is attached.

Thus, using magnetic forces, the first and second bars 420, 430 may be controlled in two ways. First, the effective inner circumference of the bars can be changed in order to alter the effective circumference of the annulus. For example, referring to FIG. 11, the effective inner circumference of first rod 420 may be reduced when a first magnetic force 510 (sometimes called a horizontal force) causes attraction of first end 424 and second end 426 of first rod 420, thereby narrowing gap 515. Second, a second magnetic force 520 (sometimes called a vertical force) can be used to keep first bar 420 and second bar 430 in place when positioned on the valve annulus such that the annulus is mechanically engaged. In addition, the distance between the bars may be adjusted using the vertical magnetic force. In at least some embodiments, additional ferromagnetic bars are placed within first bar 420 and second bar 430 in a vertical position to strengthen second magnetic force 520 (see FIG. 9A).

The magnetic forces 510, 520 are controlled by the magnetic dipoles. Even after the electric current is turned off, residual magnetic forces will remain. The magnitude of the residual magnetic force depends on the magnetic material that is used.

Referring again to FIG. 9B first catheter 490 is used to deliver first rod 420 into the heart and to position first rod 420 at a proper position near the mitral valve. Second rod 430 may also be delivered through first catheter 490, although second rod 430 may instead be delivered through a second catheter (not shown). Specifically, when placing first rod 420 on a first side of a mitral valve annulus (not shown) and placing second rod 430 on a second side of the annulus, one catheter may be used to deliver one of the rods using the trans-septal approach and the other catheter may be used to deliver the other rod through the aorta in a retrograde manner. In other words, either of the first or second rods may be delivered through either of the first or second catheters, so long as the rods are configured for delivery through the catheters (e.g., is properly sized).

Permanent magnets may be used in the embodiments disclosed herein. In at least some embodiments, the permanent magnetic materials are selected to be thin, smooth ferromagnetic bars. Saturation hysteresis loop is an important feature for these permanent magnet materials. During the process of magnetizing the sample, the magnet is subjected to a field that produces a flux density close to saturation. When the magnetizing field is reduced to zero, the induction drops back to the original value. If the magnetizing field is reversed, the magnetic poles of the thin, smooth ferromagnetic bars are reversed.

A frequently used criterion of quality of a permanent magnet is the (BH)max product. This is the maximum value that can be obtained by multiplying the corresponding B and H values at the point of operation on the demagnetization curve. B is the magnetic flux density and H is the magnetic field strength. Here, H is directly created by the electric current, I, in the magnetic circuits. The magnetomotive force, F, is decided by the magnetic flux (BA) and the distance, D, between the attractive magnetic poles.

With a wide variation of properties available in permanent magnet materials, the following criteria may be considered in selecting the optimum material for the current application: 1) Application-Magnetic Field Requirement, 2) Physical or Mechanical-Space Factor, Weight, 3) Stability Requirements, 4) Ductility Requirements, 5) Biocompatibility and 6) Cost. Dependent on the therapeutic situation, various embodiments are envisioned which emphasize different criteria.

Figure 12:
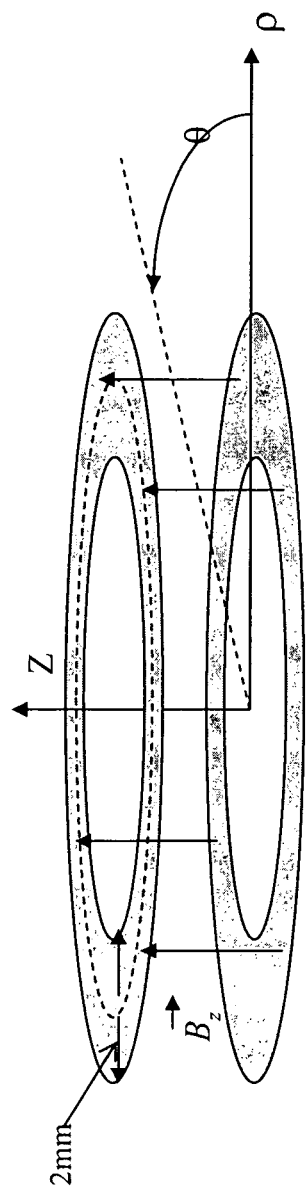
FIG. 12 shows a depiction of another embodiment of a system for remodeling a valve annulus, as disclosed herein.

The vertical force, which is the force holding the two rods together in engagement with the valve annulus, may be computed in a number of ways. For example, referring to FIGS. 12 and 13, the Maxwell's stress tensor can be written as follows:

$$T_{ij} = \frac{1}{\mu}\left[B_i B_j - \frac{1}{2}B^2 \delta_{ij}\right] \quad [1]$$

Where:
μ=permeability
$B_i$=the magnetic field in the ith axis
$B_j$=the magnetic field in the jth axis
B=the magnetic flux density
$\delta_{ij}$=the Kronecker delta.

Since only $B_z$ exists, the Maxwell's stress tensor can be written as:

$$T_{ij} = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \quad [2]$$

The stress tensor vector which is normal to the surface in two-dimensional coordinates has the form:

$$P = \begin{bmatrix} -\frac{|B_z|^2}{2\mu} & 0 & 0 \\ 0 & -\frac{|B_z|^2}{2\mu} & 0 \\ 0 & 0 & \frac{|B_z|^2}{2\mu} \end{bmatrix} \begin{pmatrix} 0 \\ 0 \\ n_z \end{pmatrix} = \frac{|B_z|^2}{2\mu} \quad [3]$$

It should be noted that the present equations are presented as merely one example of how the calculations may be carried out. They are by no means meant to be limiting and additional embodiments may be carried out by other calculations as well, as would be apparent to one having ordinary skill in the art after consideration of the present disclosure.

In at least some embodiments, the distance between the two rods is small (approximately 3 to 5 mm), the fringe loss of magnetic flux density may be negligible. The magnetic flux density B plays a significant role in the computation of attractive forces.

For example, a top magnetic bar may consist essentially of polymer-bonded neodymium-iron-boron (Nd—Fe—B) magnets formed by compression molding, in which magnet powders are mixed with a polymer carrier matrix, such as epoxy, which then solidifies to give shape to the magnetic material. Consequently, the top magnetic bar has residual induction Br (0.6-0.65 Teslas or 6000-6500 Gauss). The bottom magnetic bar may consist of a Heusler alloy, such as $Fe_{80}B_{20}$, which has the saturation magnetic flux density of 0.1257 Teslas (1257 Gauss). Similarly, it may consist of carbon-coated metal particles, which have saturation magnetization exceeding about 120 emu/g (saturation magnetic flux density≅0.15 Teslas). Therefore, it can be assumed that the bottom magnetic bar has magnetic flux density $|B_z|$=0.1 T. When $|B_z|$=0.1 T, the pressure on the bottom magnetic bar can be calculated as follows:

$$P = \frac{|B_z|^2}{2\mu} = \frac{0.1^2}{8\pi \times 10^{-7}} = 3.98 \text{ (KPa)} \quad [4]$$

When area=50 $cm^2$=50×$10^{-4}$ $m^2$, the attractive magnetic force on the bottom magnetic bar may be calculated as follows:

$$F = P \times \text{area} = 3.98 \times 10^3 \times 50 \times 10^{-4} = 20 \text{(Newton)} \quad [5]$$

From Newton's Third Law, it is known that the attractive magnetic force on the top magnetic bar is also 20 N.

Figure 13:
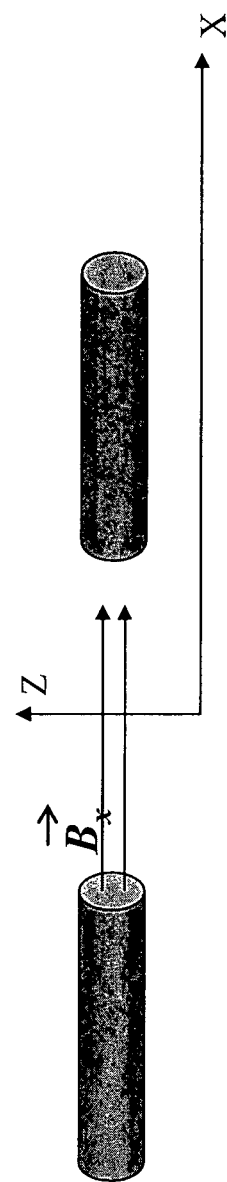
FIG. 13 shows a depiction of a horizontal magnetic force between two bars, as disclosed herein.

In addition, the horizontal force, which is the force determining the circumferential size of the bar (and therefore the size of the annulus), may be computed in a number of ways. Referring to FIG. 13, when only $B_Z$ is considered, equation [3] can be changed as:

$$P = \begin{bmatrix} \frac{|B_x|^2}{2\mu} & 0 & 0 \\ 0 & -\frac{|B_x|^2}{2\mu} & 0 \\ 0 & 0 & -\frac{|B_x|^2}{2\mu} \end{bmatrix} \begin{pmatrix} n_x \\ 0 \\ 0 \end{pmatrix} = \frac{|B_x|^2}{2\mu} \quad [6]$$

The fringe loss of magnetic flux density is assumed to be 0.5. For example, the left magnetic bar is comprised of polymer-bonded Nd—Fe—B magnets and the right magnetic bar is comprised of Heusler alloy or carbon-coated metal particles. When $|B_z|$=0.1×0.5=0.05 T, the pressure on the left and right magnetic bars can be calculated as follows:

$$P = \frac{|B_x|^2}{2\mu} = \frac{0.05^2}{8\pi \times 10^{-7}} = 1.0 \text{ (KPa)} \quad [7]$$

When area=π×$(10\times10^{-3})^2$=3.14×$10^{-4}$ $m^2$, the maximum attractive magnetic force on the left and right magnetic bars may be calculated as follows:

$$F = P \times \text{area} = 1.0 \times 10^3 \times 3.14 \times 10^{-4} = 0.314 \text{(Newton)} \quad [8]$$

In at least some embodiments, the effective circumference of the annulus may be adjusted manually. In such embodiments, instead of placing a rod on the inferior face of the valve, as described herein, an adjustable ring is placed around the annulus and is tightened to restrict the size of the circumference of the annulus.

Figure 14:
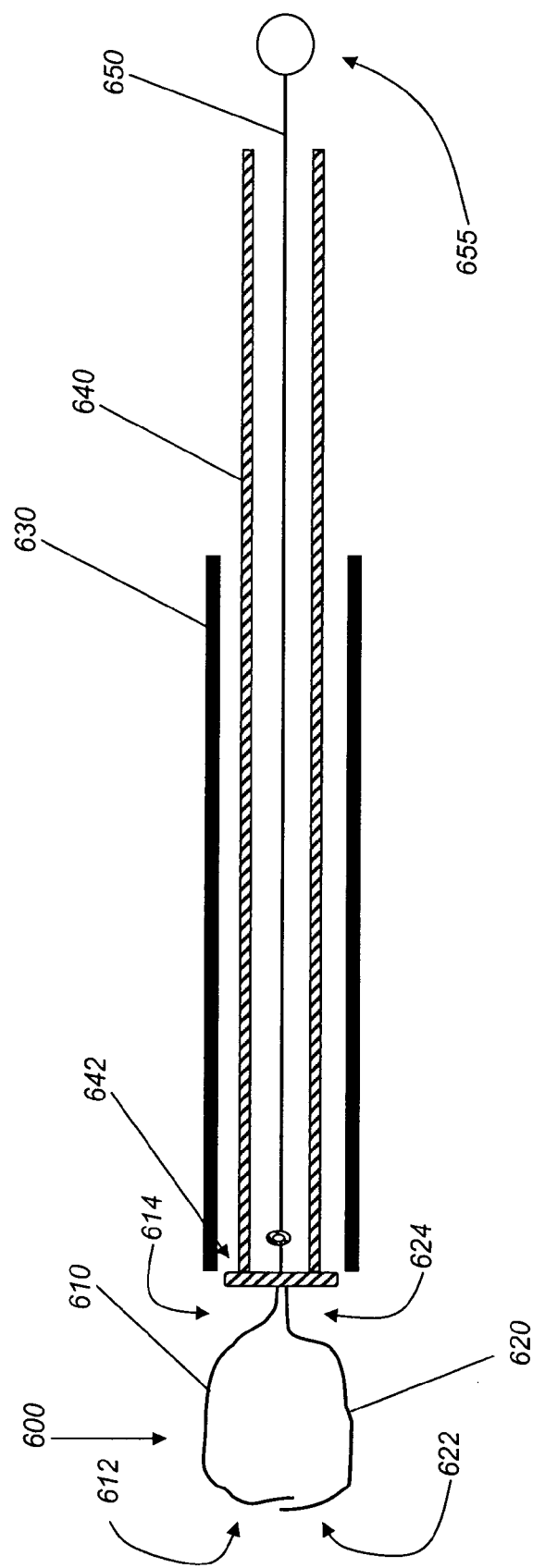
FIG. 14 shows a partial cross-sectional view of an embodiment of a system for remodeling a valve annulus, as disclosed herein.

For example, referring now to FIG. 14, there is shown a ring 600 comprising a first finger 610 and a second finger 620. First finger 610 has a distal end 612 and a proximal end 614, and second finger 620 has a distal end 622 and a proximal end 624. Fingers 610 and 620 are each shaped to fit within, and be deployed through, a delivery or sheath catheter 630. Once deployed, however, fingers 610, 620 form ring 600 to encircle a valve annulus (such as annulus 410 shown in FIG. 9C) at the inferior face of the annulus.

Fingers 610 and 620 may be made of a shape memory alloy, such as nitinol. Thus, they are relatively straight when deployed through delivery catheter 630. However, after introduction into the body and placement around the annulus, with each finger approaching the annulus from an opposite side, the fingers 610 and 620 form the shape of ring 600. Fingers 610 and 620 may be the same length or different lengths.

As shown in FIG. 14, proximal end 614 of first finger 610 is attached to distal end 642 of introducing catheter 640. Distal end 642 of introducing catheter 640 comprises a cinching mechanism. In the embodiment shown in FIG. 14, the cinching mechanism comprises a gear rack (not shown) on distal end 624 of second finger 620 and a hole with a ratchet (not shown) on distal end 642 of introducing catheter 640, much like a cable tie system. The cinching mechanism is attached to a first wire 650 such that the cinching mechanism causes tightening of ring 600 when first wire 650 is pulled. Specifically, distal end 624 of second finger 620 is threaded through the hole, such that the ratchet contacts the gear rack, and is connected to the distal end of wire 650. The ratchet and gear rack combination allows second finger 620 to be pulled into distal end 642 of introducing catheter 640, thereby effectively shortening ring 600, but prevents second finger 620 from being pulled out of catheter 640. In other words, the ratchet and gear rack combination functions as a one-way cinching mechanism, whereby ring 600 may be made smaller, but not larger. Thus, after ring 600 is placed around the valve annulus, wire 650 may be pulled using handle 655, effectively shortening ring 600 and restricting the effective circumference of the valve annulus.

In at least some other embodiments, one or both of first finger 610 and second finger 620 comprise a gear rack, are threaded through the hole of distal end 642 of introducing catheter 640, such that the ratchet contacts the gear rack, and are attached to wire 650. The attachment of one or both of fingers 610 and 620 to wire 650 may be by direct or indirect attachment, so long as ring 600 is effectively shortened when wire 650 is pulled.

Moreover, fingers 610, 620 may have zig-zag elements interposed along their length (not shown) that allows the circumference of ring 600 (and hence the effective circumference of the annulus) to decrease during the adjustment.

When handle 655 (and therefore wire 650) is pulled to shorten ring 600, introducing catheter 640 must be held stationary to counter the pulling force on wire 650. In at least some embodiments, distal end 642 of catheter 640 may comprise a pill-like structure (not shown) against which introducing catheter 640 is forced. The pill-like structure may serve as an anchor through which the wire is pulled to shorten the circumference of ring 600.

After the desired deployment of ring 600, wire 650 may be twisted off to disconnect ring 600 from the remainder of the apparatus.

Figure 15:
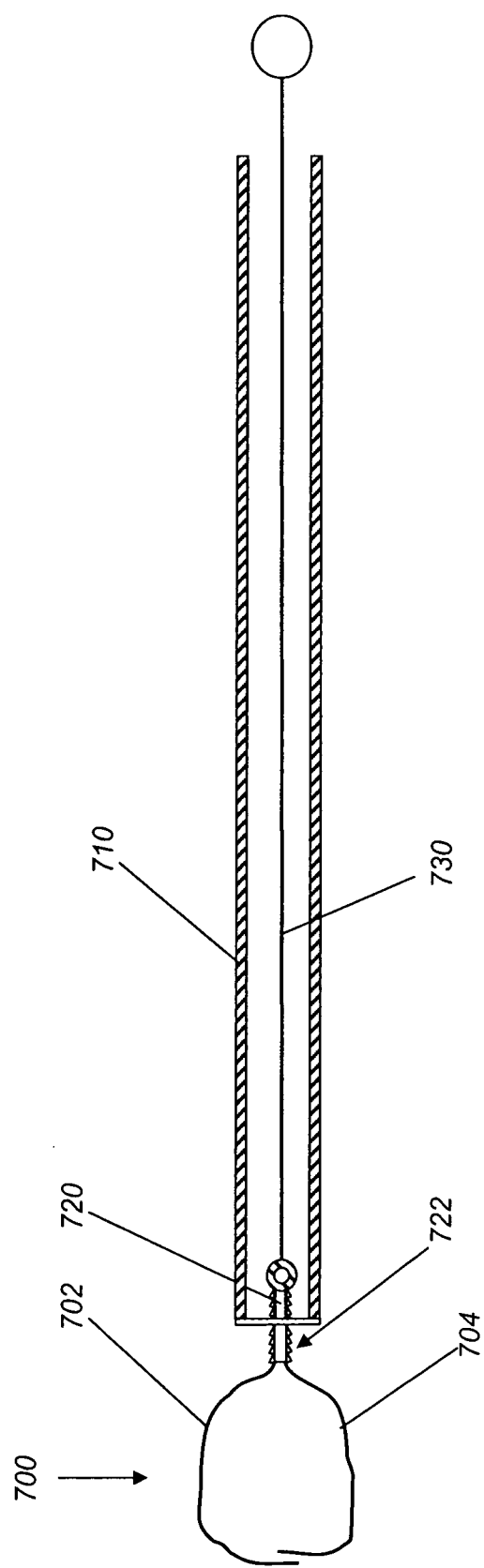
FIG. 15 shows a partial cross-sectional view of another embodiment of a system for remodeling a valve annulus, as disclosed herein.

Although the embodiment shown in FIG. 14 has a cinching mechanism comprising a gear rack and ratchet, other embodiments may use different types of cinching mechanisms. For example, FIG. 15 shows a ring 700 comprising fingers 702 and 704, an introducing catheter 710, and a wire 720 threaded through introducing catheter 710. Fingers 702 and 704 are attached to strip 730, which is attached to wire 720. In this embodiment, the cinching mechanism comprises a type of clicking mechanism, wherein the distal end of introducing catheter 710 comprises a narrow hole through which strip 720 is threaded. Strip 720 comprises catches 722 that engage with the hole to allow strip 720 to be pulled into introducing catheter 710 but not to be pulled in the other direction. Therefore, the circumference of ring 700 may be reduced by pulling wire 730, but the ring cannot be expanded.

Figure 16:
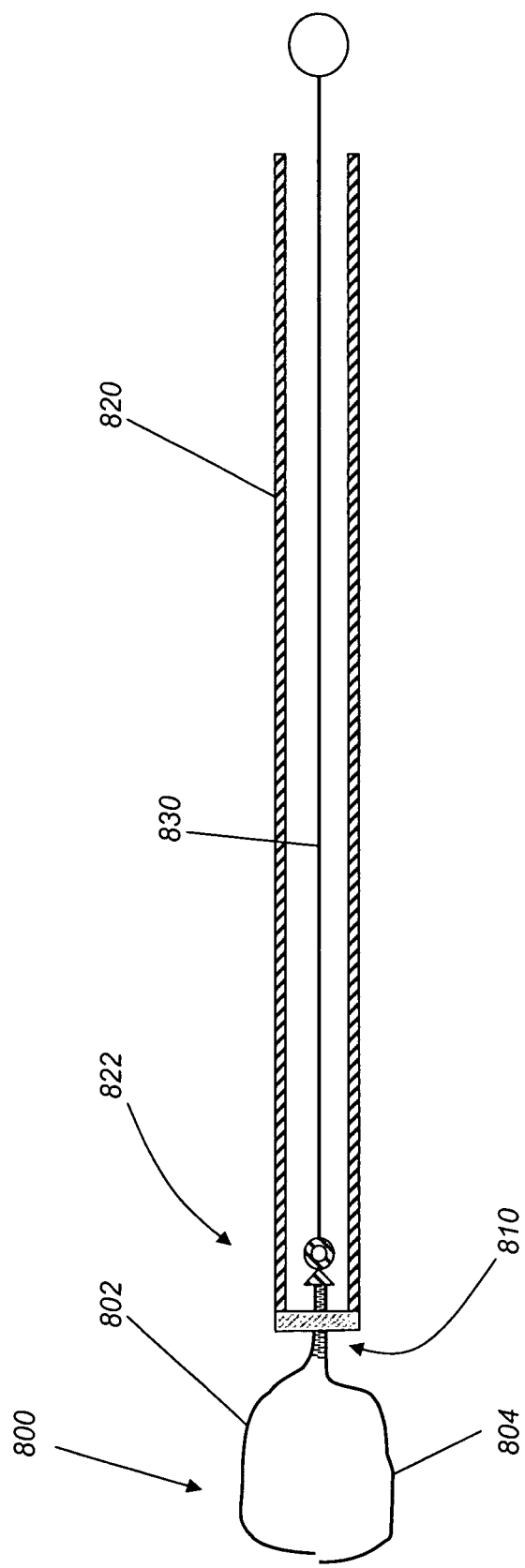
FIG. 16 shows a partial cross-sectional view of yet another embodiment of a system for remodeling a valve annulus, as disclosed herein.

As another example, FIG. 16 shows yet another embodiment of a cinching mechanism. In this embodiment, ring 800 comprises fingers 802 and 804, which are attached to a zipper 810. Zipper 810, which is attached to wire 830, includes a zipping mechanism on distal end 822 of introducing catheter 820. Consequently, as wire 830 is pulled, zipper 810 closes fingers 802 and 804, thereby restricting the effective circumference of ring 800.

A number of methods for remodeling a valve annulus are disclosed herein. For example, at least one embodiment comprises introducing into a heart a first rod and a second rod (such as first rod 420 and second rod 430 shown in FIG. 9A). As mentioned, the clinician can introduce the rods into the heart in several ways. If the rod is to be placed above the annulus, then the rod may be introduced via catheter using the trans-septal approach. If the rod is to be below the annulus, the rod may be introduced via catheter by extending the catheter, for example, through the aorta in a retrograde fashion. The rods are relatively straight when introduced through the catheter, but they form their treatment shape after deployment.

After the first rod is introduced into the heart, it may be positioned onto a first face of the annulus, which is generally either a superior face above the valve (such as superior face 412 shown in FIG. 9C) or an inferior face below the valve (such as inferior face 414 shown in FIG. 9C). The first rod is positioned around the opening of the valve on the annulus such that the first rod is capable of being anchored to the annulus face. The second rod is then positioned on the second face of the annulus.

The first and second rods are mutually anchored to the annulus (on opposing sides) via magnetic attraction to each other. The first rod may be anchored to the first face with magnetic engagement of the first rod and the second rod; the second rod is likewise anchored. In other words, referring to FIG. 9C, when first rod 420 and second rod 430 come into proximity on opposing sides of annulus 410, they will be magnetically engaged and anchored on faces 412 and 414, respectively. FIG. 9C shows first rod 420 above annulus 410 and moving downward to be anchored to face 412 of annulus 410. It also shows second rod 430 below annulus 410 and moving upward to be anchored to face 414 of annulus 410.

When anchoring the first and second rods, the rods may be positioned such that each of the vertical ferromagnetic bars on the first rod (such as ferromagnetic bars 455 on first rod 410 of FIG. 9A) is aligned with a corresponding vertical ferromagnetic bar on the second rod (such as vertical magnetic bars 475 on second rod 430 of FIG. 9A). This enables vertical magnetic engagement between the rods.

Before the rods 420, 430 can be magnetically engaged, each rod must be charged. Specifically, an electric current is applied to the first wire (such as first wire 480 shown in FIG. 9B) coiled around the first rod and the second wire coiled around the second rod. This forms at least a first inductor on first rod 420 and at least a second inductor on second rod 430. In at least some embodiments, each of the first and second rods will comprise at least three, and more likely four to six ferromagnetic bars (such as ferromagnetic bars 440, 450, and 455 on first rod 420 and ferromagnetic bars 460, 470, and 475 shown in FIG. 9A). Thus, in such embodiments, each rod will include a plurality of inductors.

The electric current may be turned off when the regurgitation is eliminated as determined using echocardiography or other imaging. After each rod is charged, its corresponding wire may be disconnected from the power source.

Another method for remodeling a valve annulus comprises a method for remodeling a mitral valve annulus manually. Restructuring the valve annulus manually involves providing an adjustable apparatus that is capable of gradually constricting the annulus to a desired degree, as determined by echocardiography or other imaging.

The method includes introducing into a heart a rod as disclosed herein (such as first rod 420 or second rod 430 shown in FIG. 9A). The rod may be placed above the valve annulus via catheter using the trans-septal approach. It is then positioned onto the superior face of the annulus.

Two fingers (such as fingers 610 and 620 shown in FIG. 14) are then introduced into the heart using an introducing catheter (such as catheter 640) within a delivery or sheath catheter (such as catheter 630). The fingers may be placed below the valve annulus by extending the catheter, for example, through the aorta in a retrograde fashion. In positioning the two fingers, the clinician may wrap one of the fingers around a portion of the inferior face of the annulus such that the finger, when constricted, may restrict the effective circumference of the annulus. The other finger is wrapped around the remainder of the inferior face. The distal ends of the two fingers (such a distal ends 612 and 622 shown in FIG. 14) are then mutually engaged to form a ring (such as ring 600 of FIG. 14) around the valve opening.

The ring is then tightened or constricted to constrict the annulus, thereby reducing the effective circumference of the annulus, which in turn reduces mitral valve regurgitation. The ring is constricted by pulling on a wire (such as wire 650 in FIG. 14) while holding the introducing catheter to prevent dislodging the catheter. The fingers are then cinched by any of a number of cinching mechanisms, including a ratchet and gear rack mechanism (as is shown in FIG. 14), a clicking mechanism (as is shown in FIG. 15), or a zipper (as is shown in FIG. 16). The cinching mechanisms allow for tightening of the ring, but they generally do not allow for loosening of the ring. However, a zipper may permit a loosening of the ring for adjustment of the annulus circumference.

During adjustment of the annulus, the amount of constriction may be determined using any of a number of imaging methods, such as echocardiography. The imaging may therefore provide feedback to the clinician during the procedure to allow for additional adjustment of the annulus if needed.

After the ring is properly set against the annulus face, the wire may be disconnected from the ring (e.g., by twisting it off). The introducing and delivery catheters are then withdrawn from the heart.

While various embodiments of devices, systems, and methods for remodeling the annulus of a valve have been described in considerable detail herein, the embodiments are merely offered by way of non-limiting examples of the invention described herein. Many variations and modifications of the embodiments described herein will be apparent to one of ordinary skill in the art in light of the this disclosure. It will therefore be understood by those skilled in the art that various changes and modifications may be made, and equivalents may be substituted for elements thereof, without departing from the scope of the invention. Indeed, this disclosure is not intended to be exhaustive or to limit the scope of the invention. The scope of the invention is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

It is therefore intended that the invention will include, and this description and the appended claims will encompass, all modifications and changes apparent to those of ordinary skill in the art based on this disclosure.

What is claimed:

1. A system for remodeling a valve annulus, comprising:
a first rod comprising a first end, a second end, a first ferromagnetic bar at the first end, a second ferromagnetic bar at a second end, and a third ferromagnetic bar between the first end and the second end;
a second rod comprising a first end, a second end, and a first ferromagnetic bar;
a first wire having a first end and a second end, a portion of the first wire being coiled around at least a portion of the first rod; and
a second wire having a first end and a second end, a portion of the second wire being coiled around at least a portion of the second rod;
wherein the first wire and the first rod are capable of forming a first inductor and the second wire and the second rod are capable of forming a second inductor, and
wherein when the first inductor and second inductor are positioned on different sides of a valve annulus and an electric current is supplied to each of the first and second wires, a magnetic attraction between the first inductor and second inductor is created, which causes remodeling of the valve annulus.

2. The system of claim 1, further comprising:
a catheter for delivering at least one of the first rod and the second rod into a body lumen of a patient, wherein at least one of the first rod and the second rod are configured for delivery through the catheter.

3. The system of claim 2, further comprising:
a first power source operatively connected to a first wire.

4. The system of claim 3, wherein:
the valve comprises a mitral valve.

5. The system of claim 3, wherein:
the first power source comprises a first battery.

6. The system of claim 5, wherein:
the first battery is configured to supply a temporary electric current to the first wire.

7. The system of claim 3, further comprising:
a second power source operatively connected to the second wire.

8. The system of claim 7, wherein:
the second power source comprises a second battery, the second battery being configured to supply a temporary electric current to the second wire.

9. The system of claim 1, wherein:
the first rod is configured such that the first end of the first rod is positioned in proximity to the second end of the first rod and the first ferromagnetic bar of the first rod is capable of magnetic engagement with the second ferromagnetic bar of the first rod.

10. The system of claim 9, wherein:
the first rod has a substantially circular shape.

11. The system of claim 9, wherein:
the first ferromagnetic bar of the second rod is positioned at the first end of the second rod;
the second rod further comprises a second ferromagnetic bar at the second end of the second rod, and a third ferromagnetic bar positioned between the first and second ends of the second rod; and
the second rod is configured such that the first end of the second rod is positioned in proximity to the second end of the second rod and the first ferromagnetic bar of the second rod is capable of magnetic engagement with the second ferromagnetic bar of the second rod.

12. The system of claim 11, wherein:
the second rod has a substantially circular shape.

13. The system of claim 12, wherein:
the third ferromagnetic bar of the first rod is configured for magnetic engagement with the third ferromagnetic bar of the second rod.

14. The system of claim 13, wherein:
the first rod further comprises a plurality of ferromagnetic bars positioned between the first and second ends of the first rod;
the second rod further comprises a plurality of ferromagnetic bars positioned between the first and second ends of the second rod; and
the plurality of ferromagnetic bars of the first rod are configured for magnetic engagement with the plurality of ferromagnetic bars of the second rod.

15. The system of claim 1, wherein:
at least one of the first bar and the second bar comprises neodymium, iron, and boron.

16. The system of claim 1, wherein:
at least one of the first bar and the second bar comprises a Heusler alloy.

17. The system of claim 1, wherein:
at least one of the first bar and the second bar comprises $Fe_{80}B_{20}$.

18. A method for remodeling a valve annulus in a heart, comprising:
introducing into the heart a first rod comprising a first end, a second end, a first ferromagnetic bar at the first end, a second ferromagnetic bar at the second end, and a third ferromagnetic bar between the first and second ends, the first rod having at least a portion of a first wire coiled around at least a portion of it, wherein the first wire is capable of operable connection to a power source;
introducing into the heart a second rod comprising a first end, a second end, and a first ferromagnetic bar, the second rod having at least a portion of a second wire coiled around at least a portion of it;
positioning the first rod onto a first side of the annulus;
positioning the second rod onto a second side of the annulus;
anchoring the first rod and the second rod to the annulus;
applying electrical current to the first wire and the first rod to form a first inductor;
applying electrical current to the second wire and the second rod to form a second inductor;
wherein when the first inductor and second inductor are positioned on different sides of a valve annulus and an electric current is supplied to each of the first and second wires, a magnetic attraction between the first inductor and second inductor is created, which causes remodeling of the valve annulus.

19. The method of claim 18, further comprising:
disconnecting the first wire from the power source.

20. The method of claim 19, wherein the second wire is capable of operable connection to a power source; and wherein the second rod further comprises a second ferromagnetic bar at the first end, and a third ferromagnetic bar at the second end.

21. The method of claim 20, further comprising:
disconnecting the second wire from the power source.

22. The method of claim 21, wherein:
the step of anchoring the first rod and the second rod to the annulus comprises positioning the first rod and the second rod such that the third ferromagnetic bar of the first rod magnetically engages the first ferromagnetic bar of the second rod.

23. The method of claim 21, wherein:
the valve comprises a mitral valve.

24. The method of claim 23, wherein:
the first rod has a substantially circular shape; and
the second rod has a substantially circular shape.

25. The method of claim 24, wherein:
the power source comprises a battery.

26. The method of claim 25, wherein:
at least one of the first bar and the second bar comprises a Heusler alloy.

27. The method of claim 25, further comprising:
restricting the circumference of the annulus.

* * * * *